United States Patent [19]
Gruenke et al.

[11] Patent Number: 5,549,106
[45] Date of Patent: *Aug. 27, 1996

[54] INSPIRATORY AIRWAY PRESSURE SYSTEM USING CONSTANT PRESSURE AND MEASURING FLOW SIGNALS TO DETERMINE AIRWAY PATENCY

[75] Inventors: Roger A. Gruenke; Russell L. Trimble, both of Overland Park, Kans.

[73] Assignee: Puritan-Bennett Corporation, Lenexa, Kans.

[*] Notice: The term of this patent shall not extend beyond the expiration date of Pat. No. 5,134,995.

[21] Appl. No.: 95,652

[22] Filed: Jul. 21, 1993

Related U.S. Application Data

[63] Continuation of Ser. No. 846,133, Apr. 9, 1992, Pat. No. 5,259,373, which is a continuation of Ser. No. 632,327, Dec. 21, 1990, Pat. No. 5,134,995, which is a continuation-in-part of Ser. No. 518,001, May 2, 1990, abandoned, which is a continuation-in-part of Ser. No. 513,757, Apr. 24, 1990, abandoned, which is a continuation-in-part of Ser. No. 354,143, May 19, 1989, abandoned.

[51] Int. Cl.⁶ .......................... A61M 16/00; A62B 7/04; F16K 31/02; F16K 31/26
[52] U.S. Cl. ................. 128/204.23; 128/204.21; 128/204.26; 128/719
[58] Field of Search .......................... 128/204.21–204.23, 128/204.18, 716, 719, 724, 204.26

[56] References Cited

U.S. PATENT DOCUMENTS

| | | | |
|---|---|---|---|
| 3,991,304 | 11/1976 | Hillsman . | |
| 4,365,636 | 12/1992 | Barker | 128/716 |
| 4,440,177 | 4/1984 | Anderson et al. | 128/719 |
| 4,723,543 | 2/1988 | Beran | 128/207.14 |
| 5,107,831 | 4/1992 | Halpern et al. | 128/204.26 |
| 5,134,995 | 8/1992 | Gruenke et al. | 128/204.23 |
| 5,148,802 | 9/1992 | Sanders et al. | 128/204.18 |
| 5,199,424 | 4/1993 | Sullivan et al. | 128/204.18 |
| 5,203,343 | 4/1993 | Axe et al. | 128/725 |
| 5,215,082 | 6/1993 | Kallok et al. | 128/419 G |
| 5,245,995 | 9/1993 | Sullivan et al. | 128/204.23 |
| 5,259,373 | 11/1993 | Gruenke et al. | 128/204.23 |
| 5,353,788 | 10/1994 | Miles . | |

FOREIGN PATENT DOCUMENTS

| | | |
|---|---|---|
| AUAI1989/88 | 12/1988 | Australia . |
| 0046570 | 3/1982 | European Pat. Off. . |
| 91913151 | 6/1994 | European Pat. Off. . |
| 3306607A1 | 9/1983 | Netherlands . |
| 4038871A1 | 6/1992 | Netherlands . |
| WO88/10108 | 12/1988 | WIPO . |
| WO90/14121 | 11/1990 | WIPO . |
| WO91/06832 | 5/1991 | WIPO ............................. G01F 1/74 |
| WO89/10768 | 11/1994 | WIPO . |

OTHER PUBLICATIONS

Australian Industrial Property Organisation Patent Office Action dated Jan. 24, 1994 re AU 33877/93.
Southworth et al., McGraw–Hill Book Company, pp. 6–10, "Digital Computation and Numerical Methods".

(List continued on next page.)

*Primary Examiner*—Kimberly L. Asher
*Attorney, Agent, or Firm*—Fulwider Patton Lee & Utecht

[57] ABSTRACT

An apparatus and method for facilitating the respiration of a patient are disclosed which are particularly useful in treating mixed and obstructive sleep apnea and certain cardiovascular conditions, among others, by increasing nasal air pressure delivered to the patient's respiratory passages just prior to inhalation and by subsequently decreasing the pressure to ease exhalation effort. The preferred apparatus includes a patient-coupled gas delivery device for pressurizing the patient's nasal passages at a controllable pressure, and a controller coupled with the delivery device having a pressure transducer for monitoring the nasal pressure and a microcontroller for selectively controlling the nasal pressure. In operation, the controller determines a point in the patient breathing cycle just prior to inhalation and initiates an increase in nasal pressure at that point in order to stimulate normal inhalation, and subsequently lowers the nasal pressure to ease exhalation efforts.

22 Claims, 21 Drawing Sheets

OTHER PUBLICATIONS

Dupuis, R. R. T., The C.V. Mosby Company (1986), pp. 107–117 "Ventilators Theory and Clinical Application".

Ballard et al., West J Med (1986), pp. 248–250 "Sleep Apnea— Diagnosis and Treatment".

Remmers et al., Sleep and Respiration (1990), pp. 261–271 "Mechanics of the Pharynx in Patients with Obstructive Sleep Apnea".

Sanders et al., Chest (1990), pp. 317–324 "Obstructive Sleep Apnea Treated by Independently Adjusted Inspiratory and Expiratory Positive Airway Pressures Via Nasal Mask".

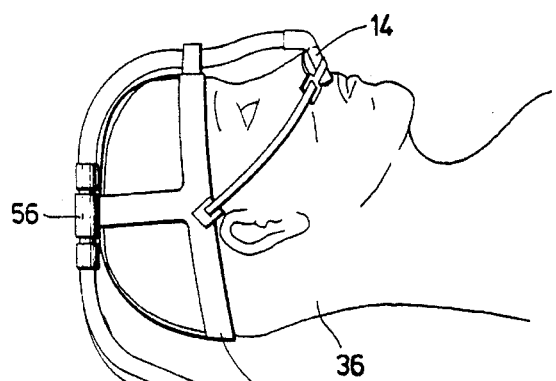
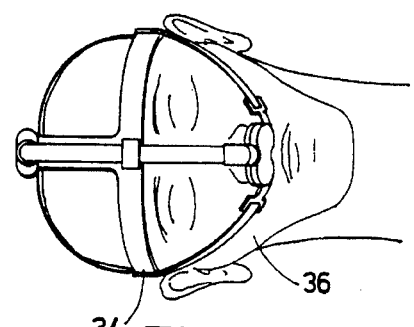
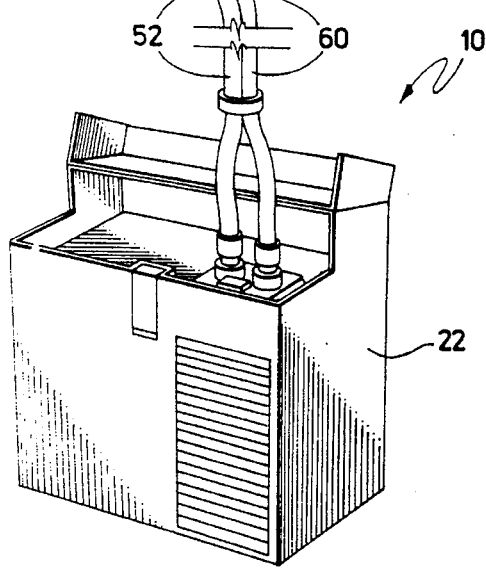
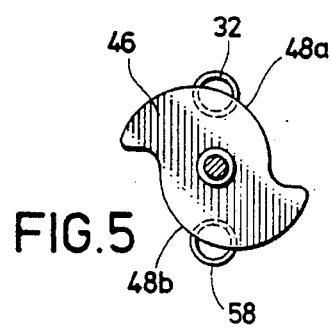
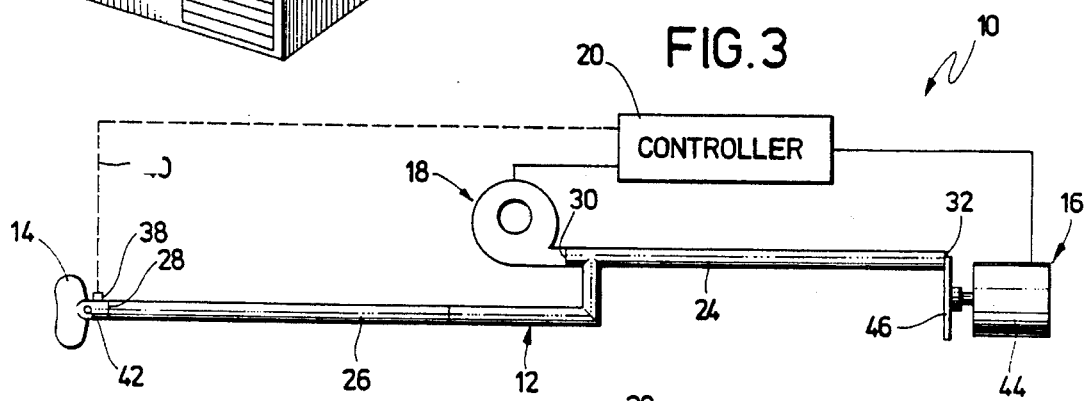
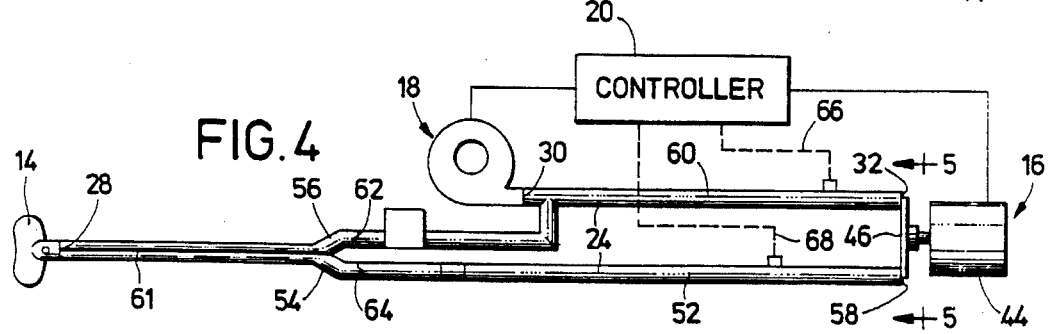

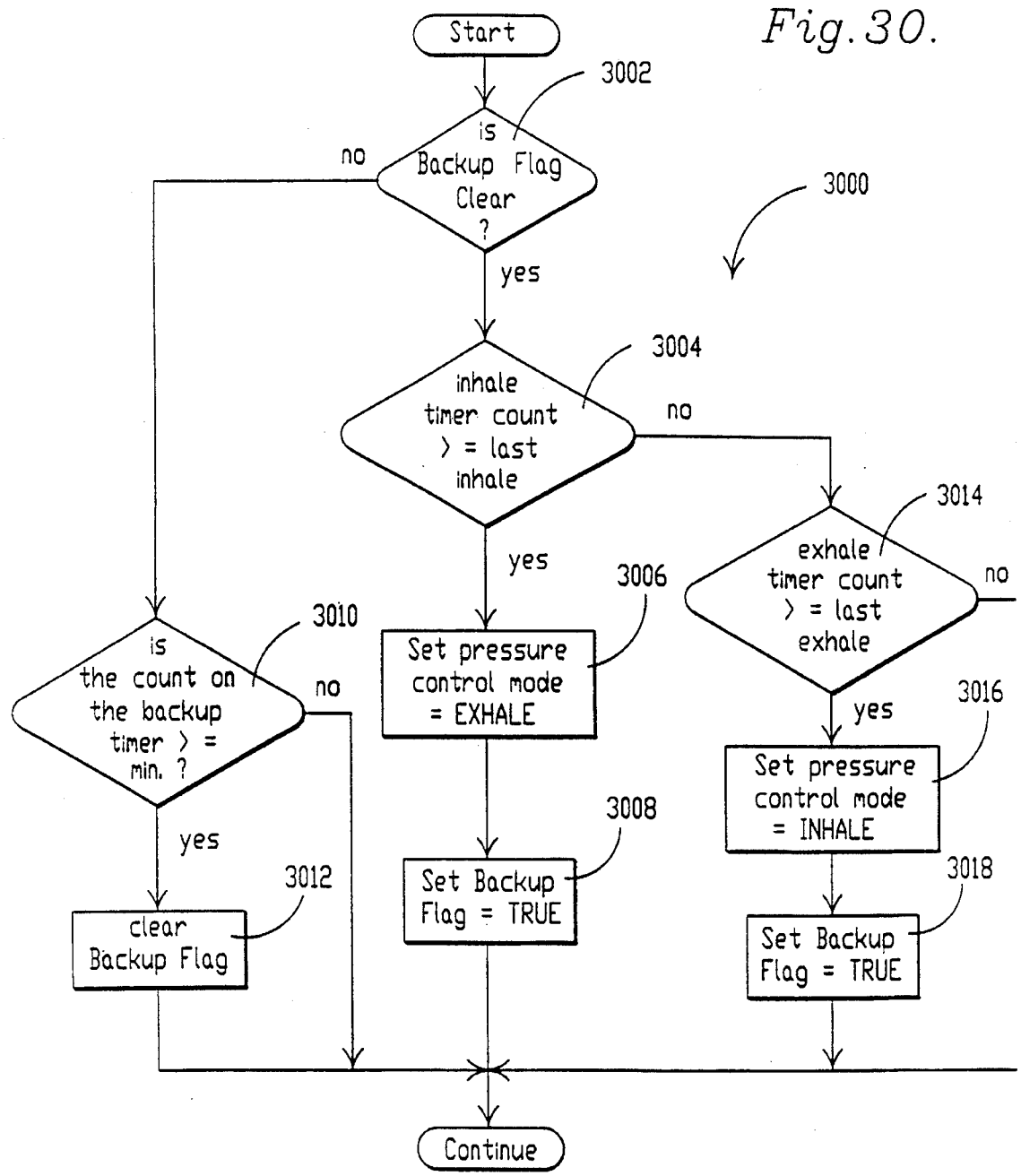

INSPIRATORY AIRWAY PRESSURE SYSTEM USING CONSTANT PRESSURE AND MEASURING FLOW SIGNALS TO DETERMINE AIRWAY PATENCY

This application is a continuation of Ser. No. 07/846,133, filed Apr. 9, 1992, now U.S. Pat. No. 5,259,373, which is a continuation of Ser. No. 07/632,327, filed Dec. 21, 1990, now U.S. Pat. No. 5,134,995, which is a continuation-in-part of Ser. No. 07/518,001 filed May 2, 1990, now abandoned which was a continuation-in-part of Ser. No. 07/513,757, filed Apr. 24, 1990, now abandoned which was a continuation-in-part of Ser. No. 07/354,143 filed May 19, 1989, now abandoned. The contents of each of these applications are hereby incorporated by reference.

BACKGROUND OF THE INVENTION

1. Field of the Invention

The present invention relates to an apparatus and method for facilitating the respiration of a patient and is particularly useful in treating disturbed breathing, snoring, mixed obstructive sleep apnea, and certain cardiovascular sleep conditions. More particularly, the present invention is concerned with an apparatus and method for imposing a positive pressure on the patient's airways just prior to the onset of inhalation in order to induce and/or permit inhalation, and for subsequently reducing the pressure on the airways to ease exhalation effort. Another aspect of the invention is concerned with monitoring sounds associated with patient's respiration and controlling the gas pressure delivered to the patient's respiratory passages in accordance with the sounds.

2. Description of the Prior Art

Obstructive sleep apnea is a sleep disorder characterized by relaxation of the airway including the genioglossus throat muscle tissue during sleep. When this occurs, the relaxed muscle can partially or completely block the patient's airway, a condition more prevalent in overweight patients. Partial blockage can result in snoring. Complete blockage can result in sleep apnea.

When complete blockage occurs, the patient's inhalation efforts do not result in the intake of air and the patient becomes oxygen deprived. In reaction, the patient begins to awaken. Upon reaching a nearly awakened state, the genioglossus muscle resumes normal tension which clears the airway and allows inhalation to occur. The patient then falls back to a deeper sleep whereupon the genioglossus muscle again relaxes and the apneic cycle repeats.

Central apnea is when no inspiratory effort occurs or is delayed. Central apnea may be combined with obstructive apnea, known as mixed apnea. Other breathing irregularities such as Cheynes Stockes breathing may have apneic intervals when intake aidlow ceases.

In some patients, sleep apnea events can occur dozens of times during the course of a sleep session. In consequence, the patient never achieves a fully relaxed, deep sleep session because of the repetitive arousal to a nearly awakened state. The patient is also deprived of REM (rapid eye movement) sleep. People afflicted with sleep apnea are continually tired even after an apparently normal night's sleep.

In order to treat obstructive sleep apnea, the so-called continuous positive airway pressure (CPAP) system has been devised in which a prescribed level of positive airway pressure is continuously imposed on the patient's airways. The presence of such positive pressure on the airways provides a pressure splint to offset the negative inspiratory pressure to maintain tissue position tension and thereby maintain an open patient airway. The positive airway connection with a patient is typically achieved by way of a nasal pillow such as that disclosed in U.S. Pat. No. 4,782,832 hereby incorporated by reference in which the nasal pillow seals with the patient's nares and imposes the positive airway pressure on the nasal passages.

The CPAP system meets with objections from patients, however, because the patient must exhale against the positive pressure. This increases the work to exhale. Some patients have difficulty getting used to this and as a result, may discontinue the therapy. Drying of the nose and airway due to continuous circulation of room air is also a complaint. Also, exhaled carbon dioxide tends to remain in some nasal masks with CPAP therapy.

In prescribing CPAP therapy, it is usually necessary for a patient to spend one or two nights in a sleep treatment laboratory where it is first determined whether the patient has a respiratory disorder such as sleep apnea. If so, the patient is then fitted with a CFAP device whereupon the required gas pressure is determined for providing the necessary air splint to maintain airway patency.

The required pressure for maintaining patency is usually higher when the patient is sleeping on his or her back than when sleeping in a side rest position. The higher pressure is usually prescribed in order to ensure sufficient pressure in all sleeping positions. The higher pressure is not needed, however, in all circumstances. For example, before the patient has fallen asleep and in the early stages of sleep, the higher pressures are not needed. Additionally, the higher pressures are often not needed during deep sleep when the patient is in the side rest position. Furthermore, a given patient may only be subject to sleep apnea under certain conditions such as when the patient is extremely tired or under the influence of alcohol or sleep-inducing drugs. As a result, the patient is subjected to the discomfort of the high prescription pressures even when not needed.

SUMMARY OF THE INVENTION

The inspiratory airway pressure system of the present invention solves the prior art problems as outlined above. More particularly, the preferred system hereof initiates inspiratory nasal air pressure just prior to inhalation in order to provide a pressure splint to offset negative inspiratory pressure and retain the normal position of the genioglossus muscle thereby ensuring an open patient airway, and subsequently reduces the pressure for ease of exhalation. Airflow during this exhalation is primarily the patient's exhalent with desirable humidity.

The preferred apparatus is adapted for connection with a patient-coupled gas delivery device for pressurizing at least a portion of a patient's respiratory passages, such as the nasal passages, with a breathable gas, preferably ambient air which may be supplemented with oxygen, at a controllable gas pressure. The apparatus includes means for determining a point in the patient's breathing cycle before the onset of an inhalation phase and subsequent to a prior inhalation phase, and further includes gas control means for initiating, at the determined point in the breathing cycle, an increase in the gas pressure toward a selected, and preferably prescribed, high pressure level. The gas control means further controls the gas pressure at the higher level during at least a portion of the inhalation phase and subsequently lowers the gas pressure in order to present a lower pressure level during at least a portion of the subsequent exhalation phase.

In preferred forms, the apparatus tracks the patient's breathing cycle, thereby determines the end of the exhalation phase of the breathing cycle, and initiates the pressure increase at that point in the breathing cycle. Alternatively, the apparatus determines an interval time as the point in the breathing cycle for increasing the inspiratory pressure as a function of previous breath rates and inhalation and exhalation intervals.

The apparatus desirably includes a controllable, variable speed blower for supplying ambient air above atmospheric pressure, a nasal pillow for coupling with the patient's nares, a conduit intercoupling the blower and nasal pillow, and a controllable, variably positionable vent valve coupled with the conduit for venting air therefrom. The preferred apparatus also includes a controller operably coupled with the blower and with the vent valve, and a pressure transducer for sensing the patient's nasal air pressure.

In operation, the controller maintains a set point pressure by varying the position of the vent valve to vent greater or lesser amounts of air from the conduit in correspondence with patient exhalation and inhalation. The controller further tracks the position of the vent valve and thereby tracks the patient's breathing cycle. That is to say, as the patient inhales during the inhalation cycle, the vent valve must close partially to maintain the pressure of the ambient air as the patient inhales. In this way, the movement of the valve corresponds to the inhalation of the patient. Similarly, during exhalation at a preferred lower pressure set point, the vent valve must vent greater amounts of ambient air from the conduit which tracks the patient's exhalation phase. By such tracking, even at different set point pressures, the system hereof is able to increase the set point pressure predictably prior to the onset of inhalation, and to subsequently decrease the pressure during the next exhalation phase.

In another aspect of the invention, sounds and pressure variations associated with a patient's respiratory passages are monitored and the set point pressure of the gas delivered to the patient's airways is varied in accordance with the monitored sounds. This aspect of the invention takes advantage of the fact that snoring sounds typically precede the onset of obstructive sleep apnea. That is to say, sleep apnea and snoring sounds can be considered varying degrees of the same phenomenon in which the upper airway muscles may progressively relax resulting in vibration of the partially relaxed air passage, and then may progress to obstruction of the air passage when the upper airway muscles relax completely. By monitoring airway sounds, and in particular snoring sounds, the applied pressure can be raised before an apneic event occurs and thereby prevent the occurrence.

In another embodiment of the invention hereof, an apparatus and method are disclosed for determining the airway patency of a patient and for quantifying that patency. By knowing the patient airway patency, the airway pressure applied to the patient can be optimized to aid respiration and minimize discomfort associated with excessive pressure. That is to say, by determining patient airway patency, patient respiration can be better characterized in some circumstances than by monitoring airway sounds. Other preferred aspects of the present invention hereof are explained further hereinbelow.

BRIEF DESCRIPTION OF THE DRAWING FIGURES

FIG. 1 is a plan view of the head of a sleeping patient shown wearing the preferred patient-coupling head gear for use with the present invention;

FIG. 2 is a side elevational view of the patient's head and head gear of FIG. 1 shown coupled with the preferred housing cabinet of the dual conduit embodiment of the present invention;

FIG. 3 is a schematic representation of the single-conduit embodiment of the present invention;

FIG. 4 is a schematic representation of the dual-conduit embodiment of FIG. 2;

FIG. 5 is an elevational view of the preferred vent valve element in position over the vent ends of the dual-conduit embodiment of FIG. 4;

Figure 13:
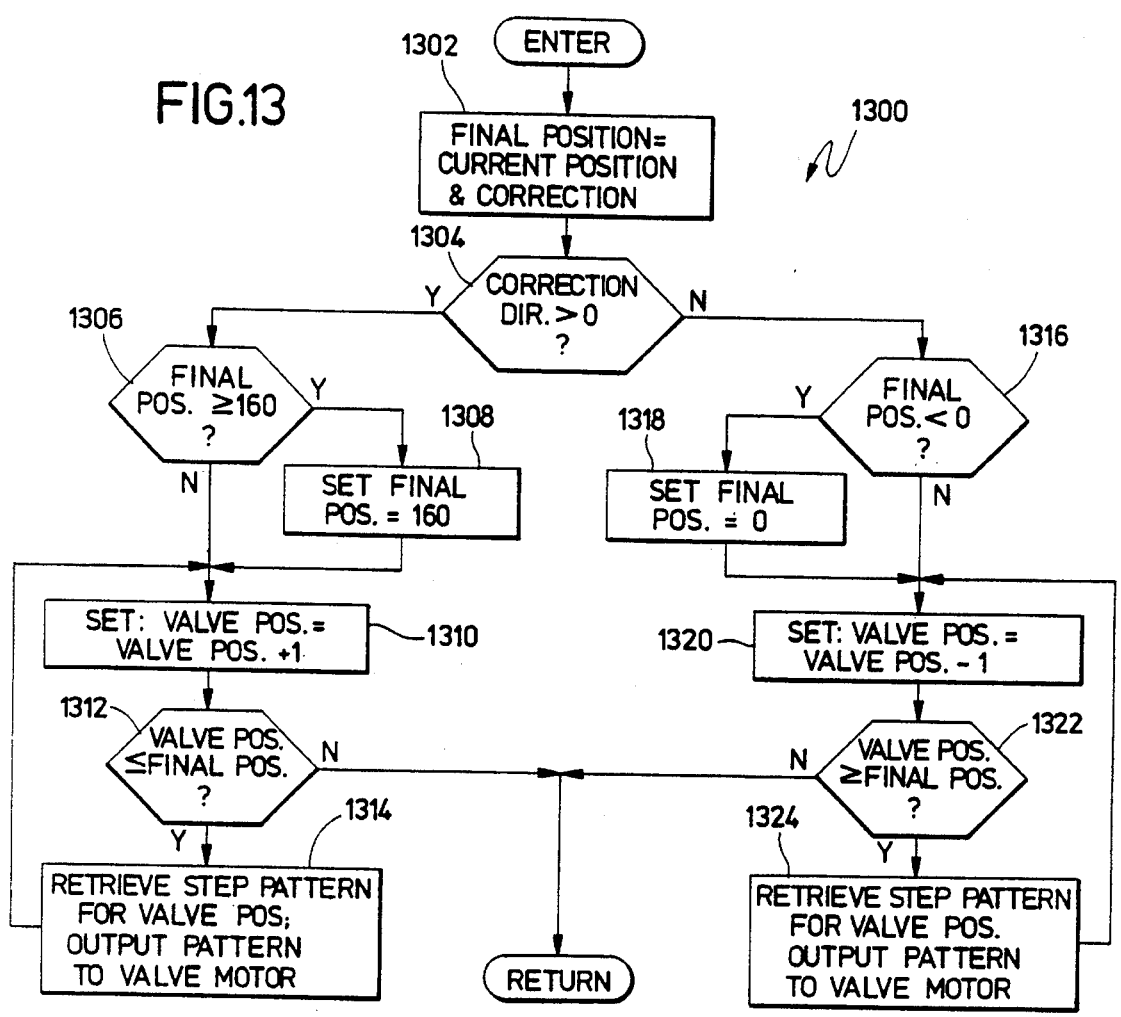
Figure 6:
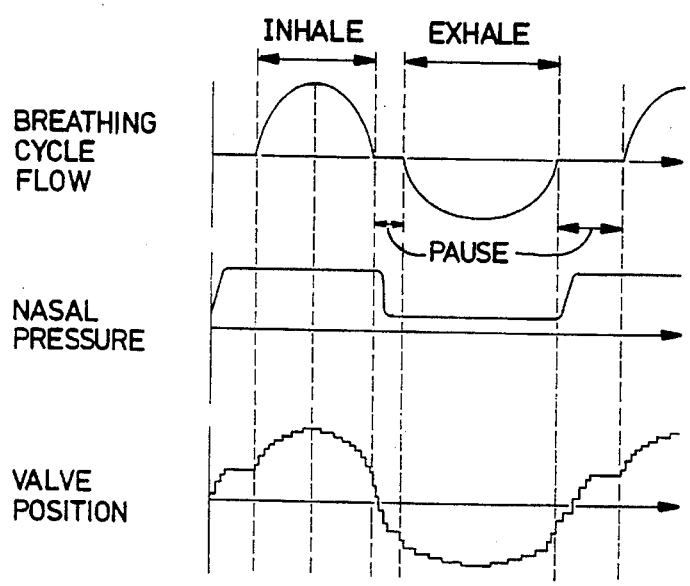
Figure 7:
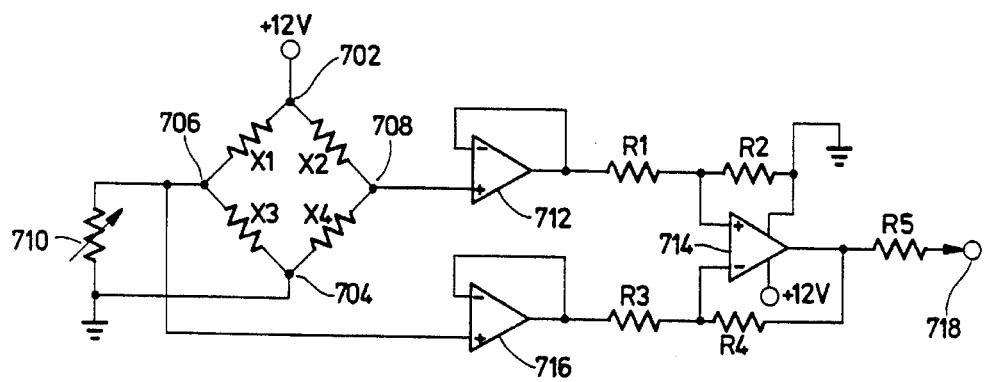
Figure 11:
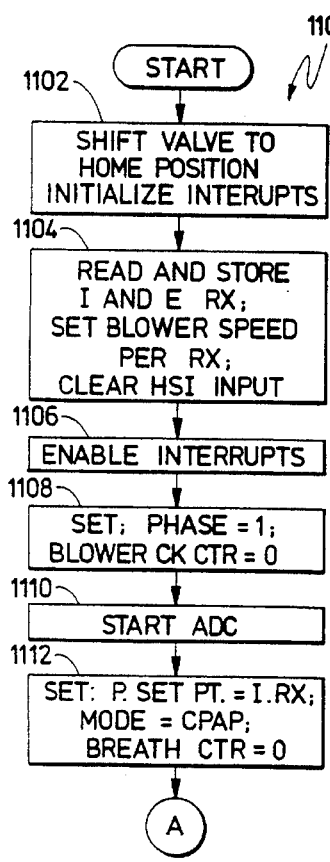
Figure 14:
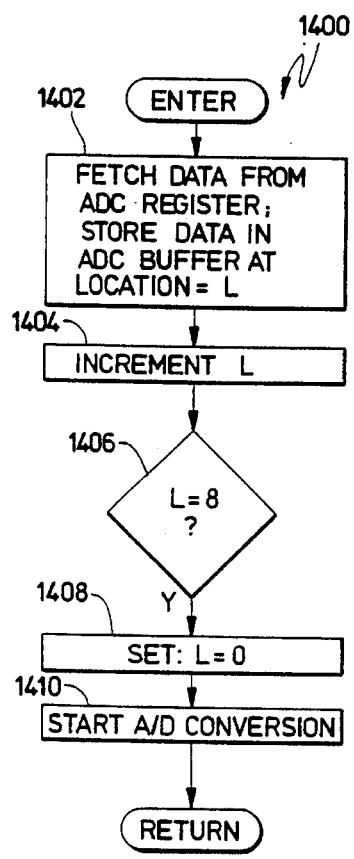
Figure 15:
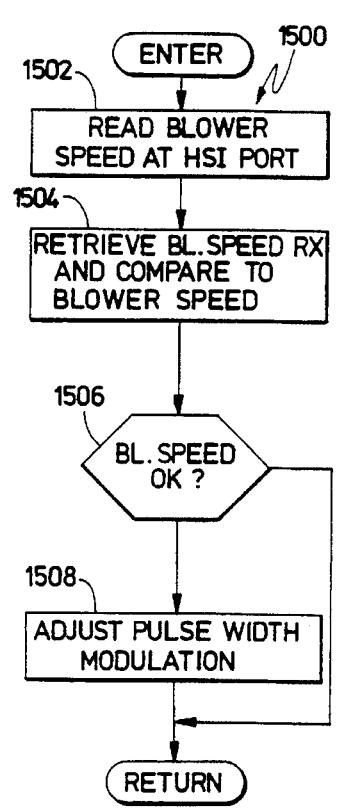
Figure 8:
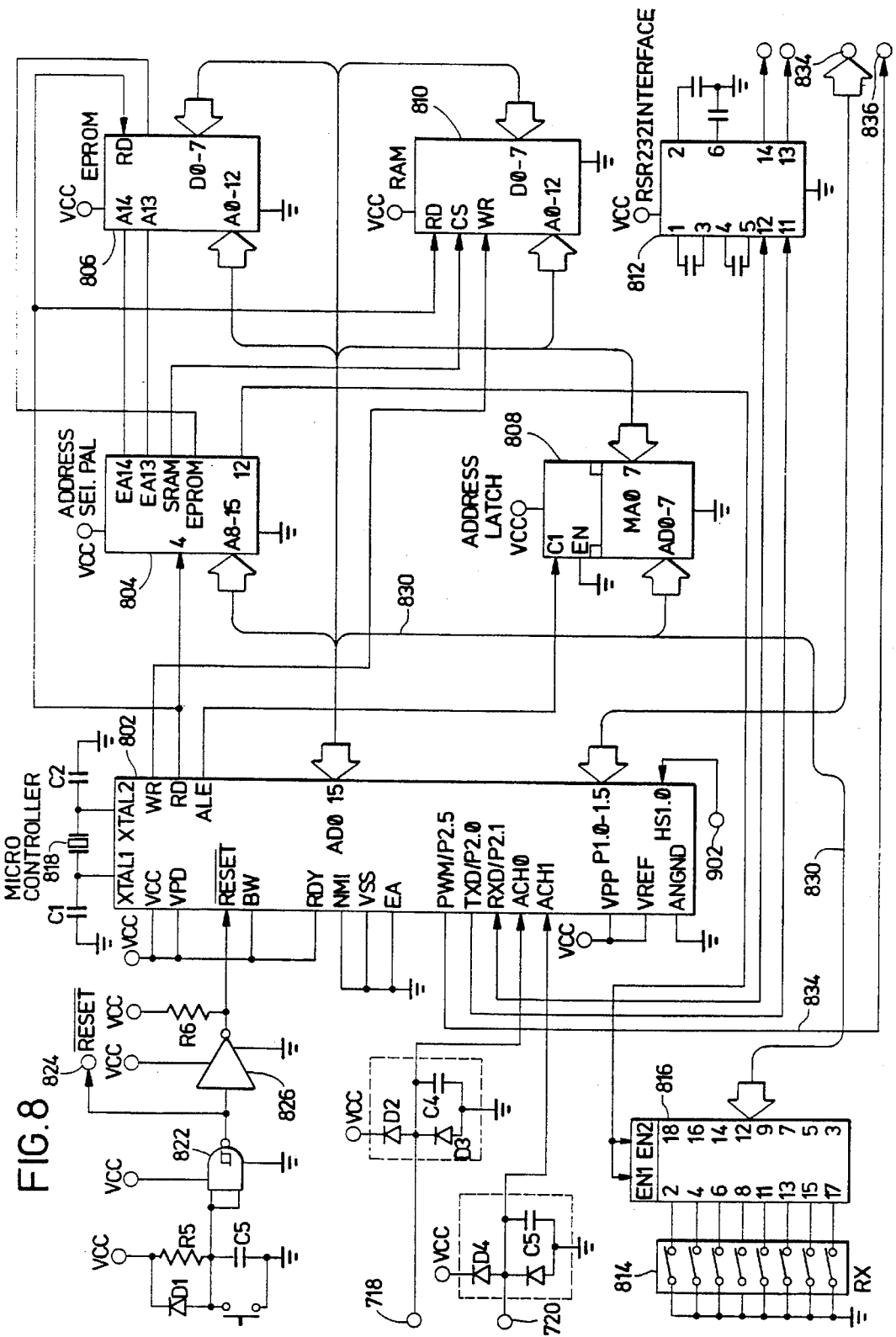
Figure 10:
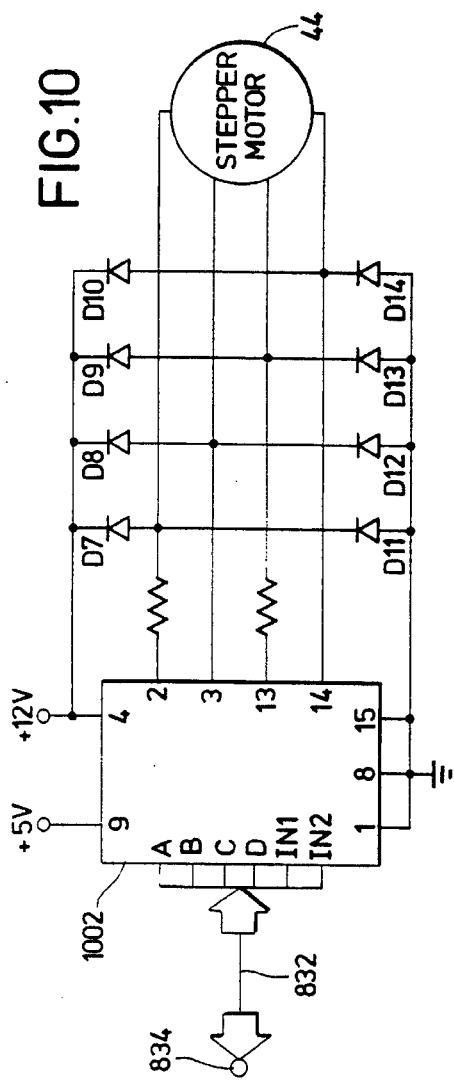
Figure 9:
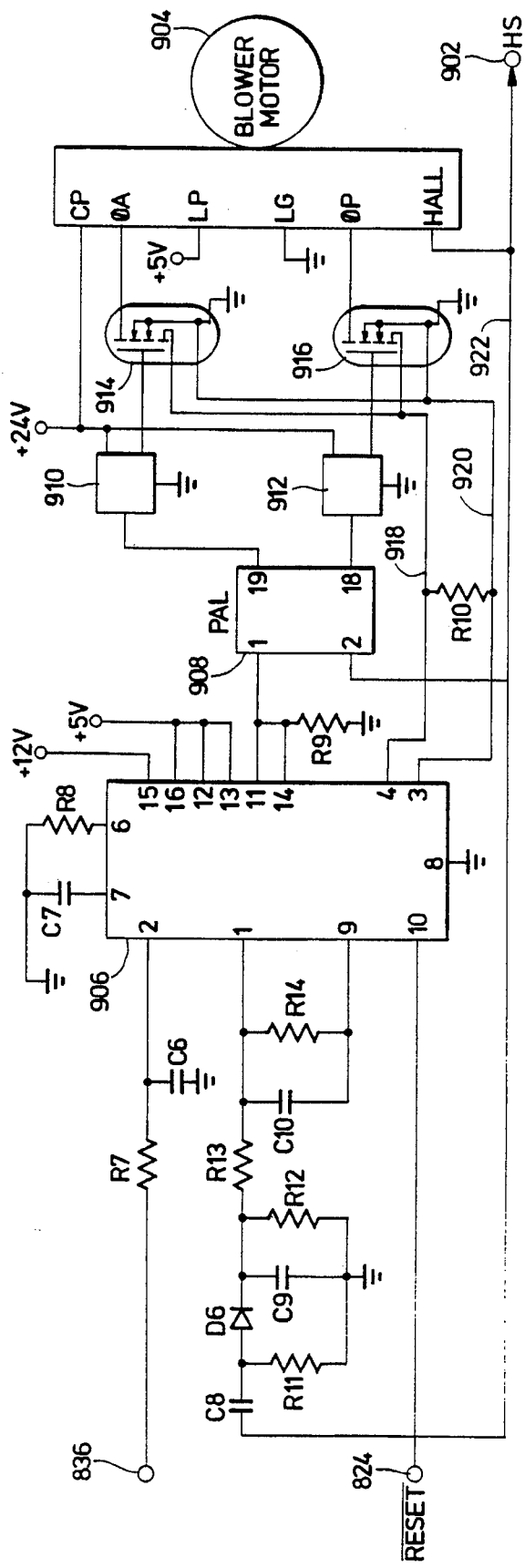
Figure 12:
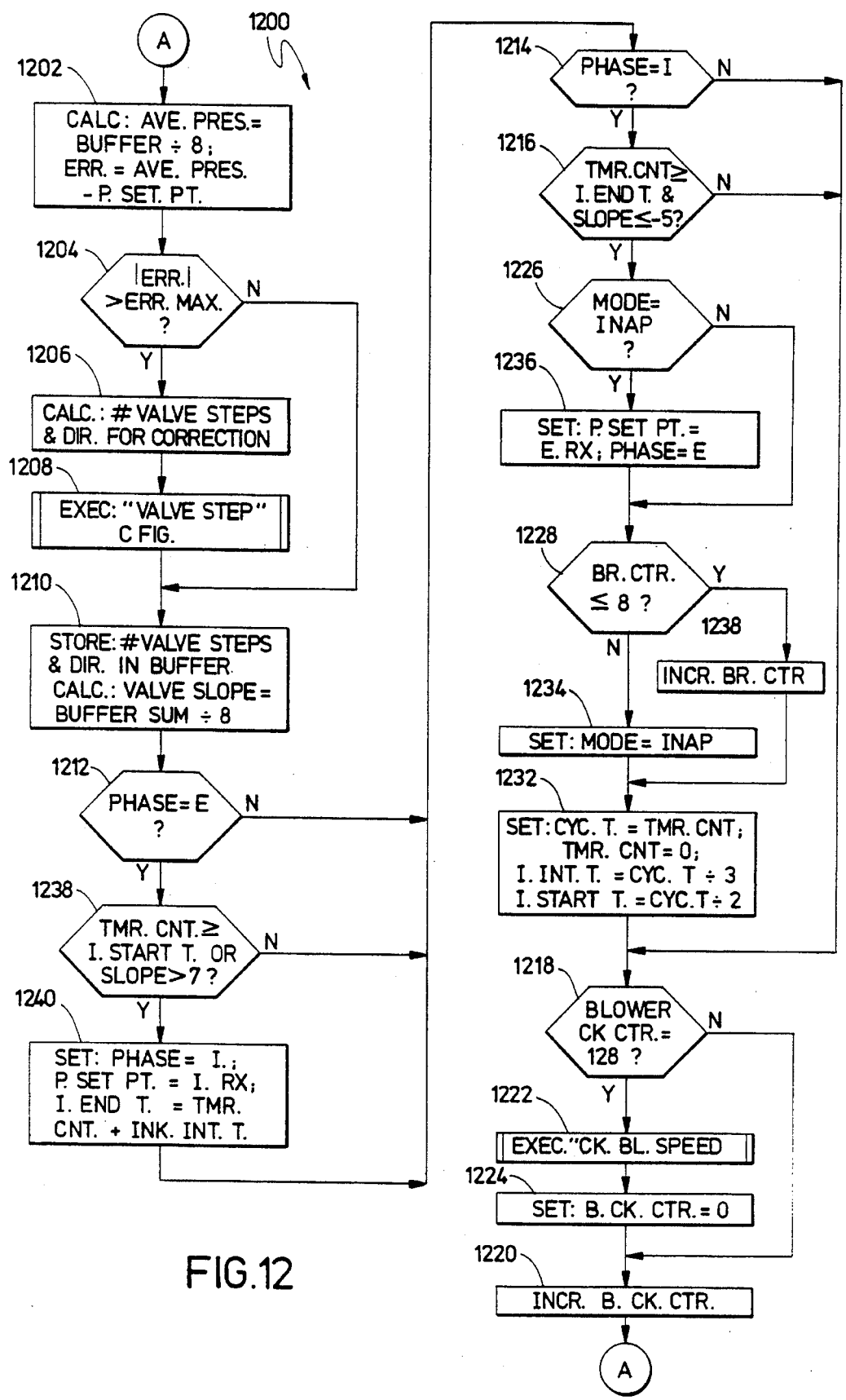
Figure 16:
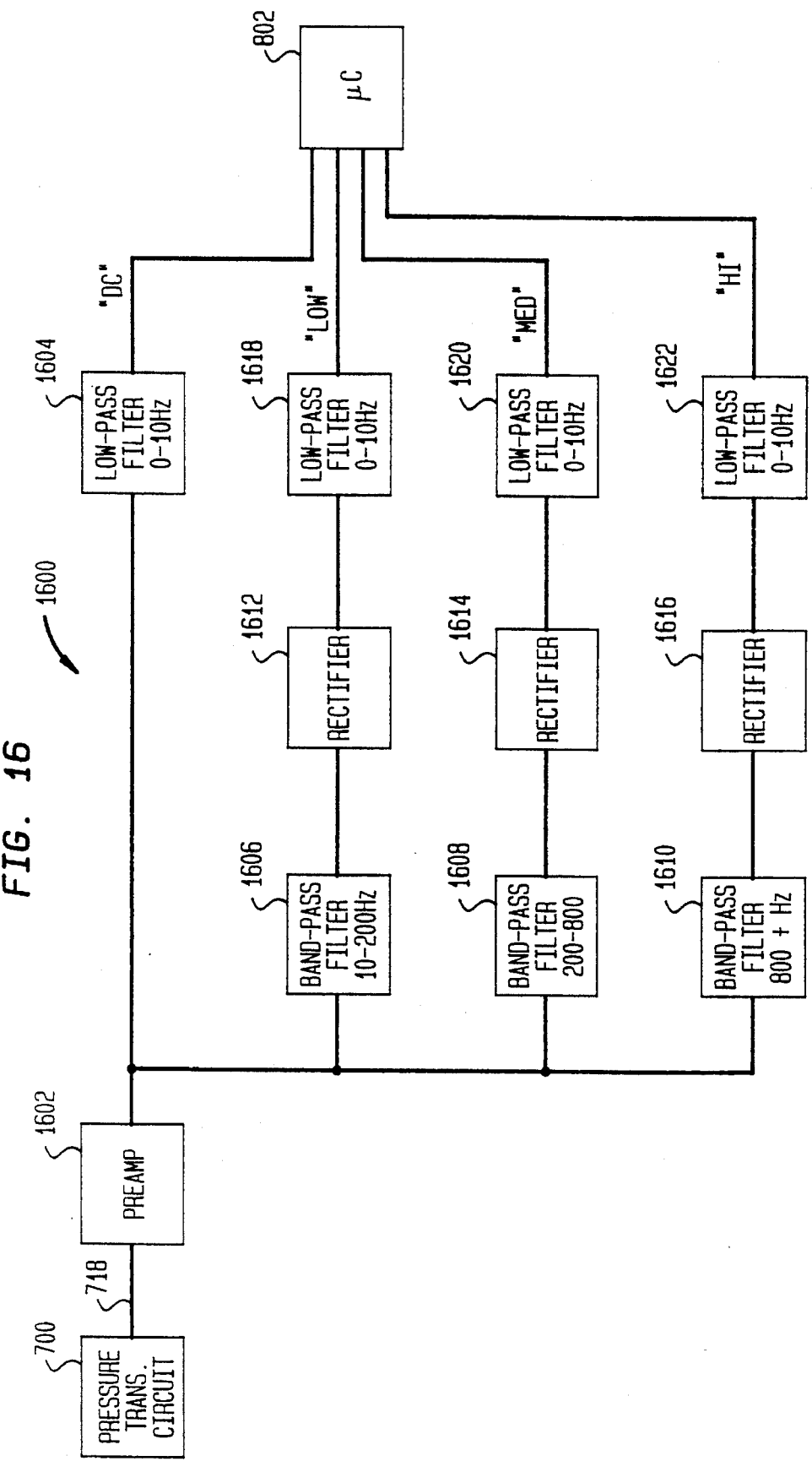
Figure 17:
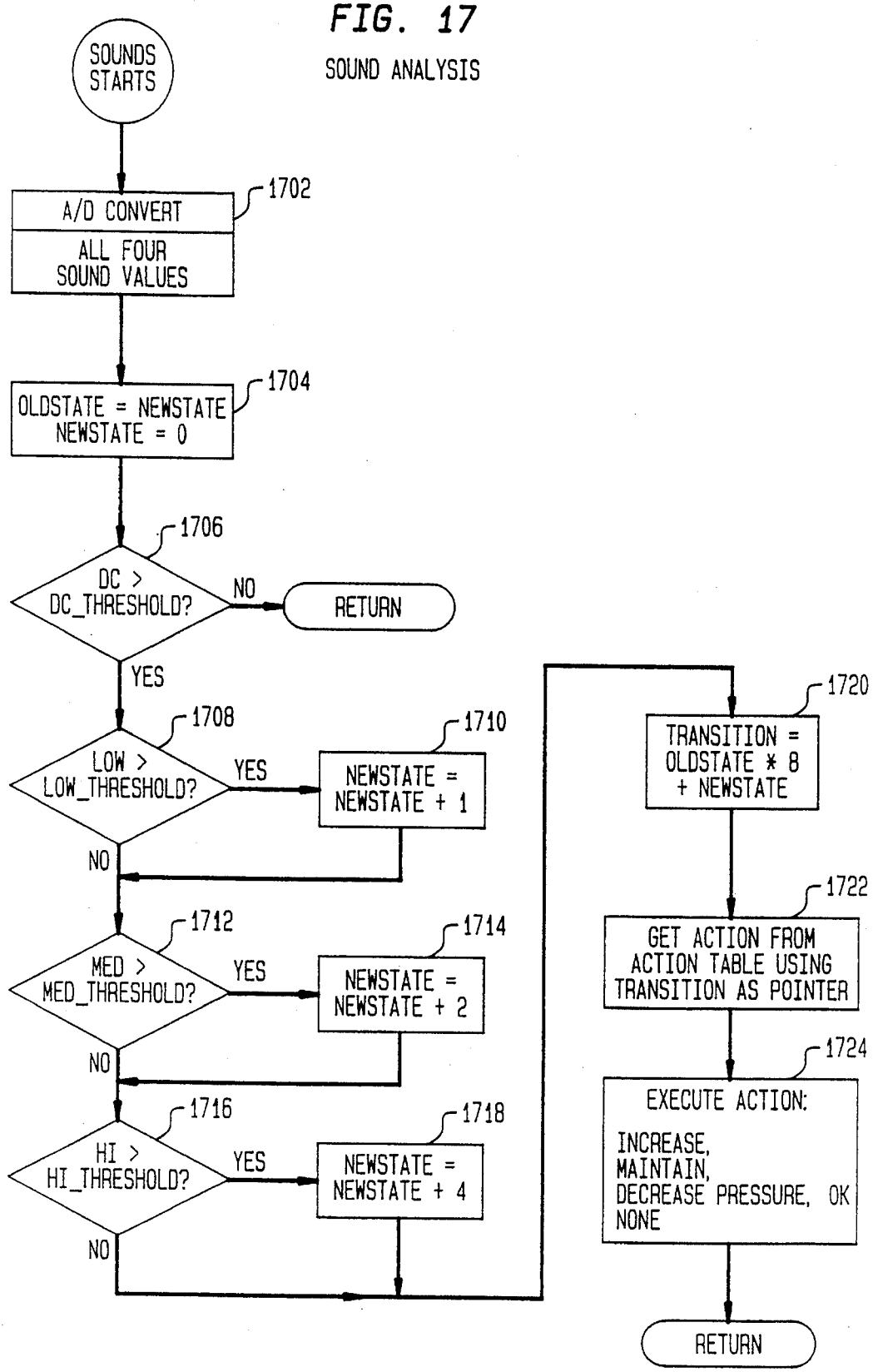
Figure 18:
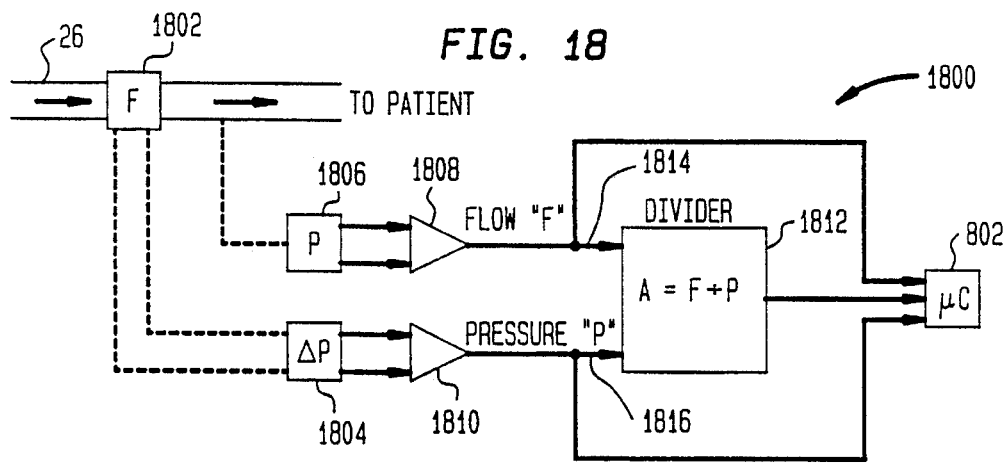
Figure 19:
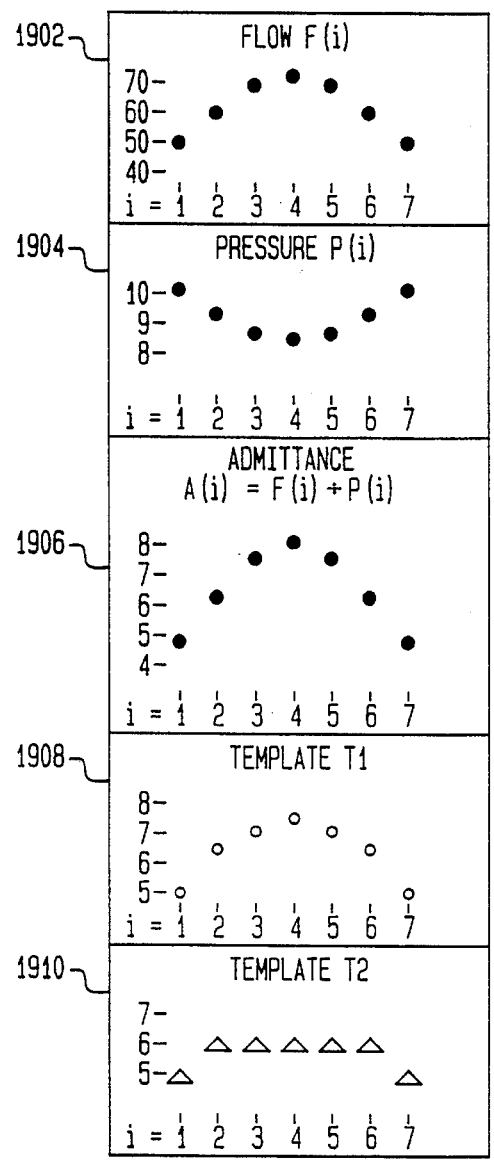
Figure 20:
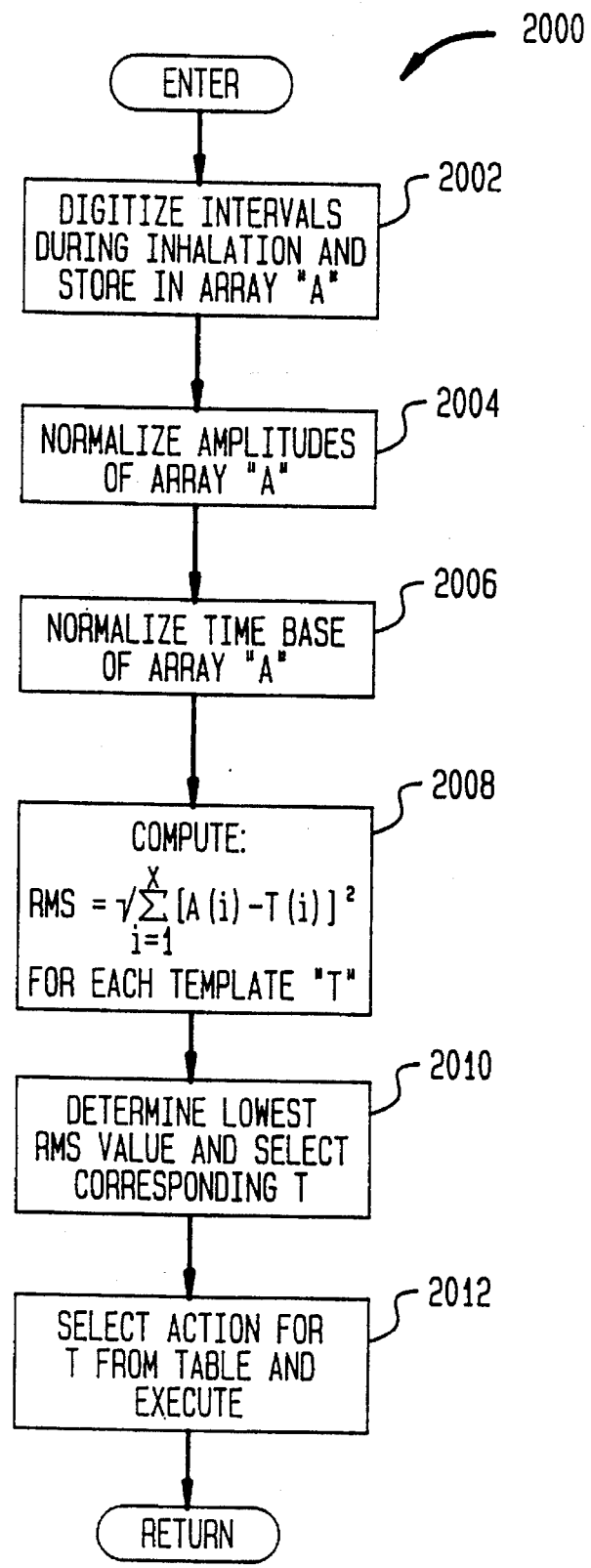
Figure 21:
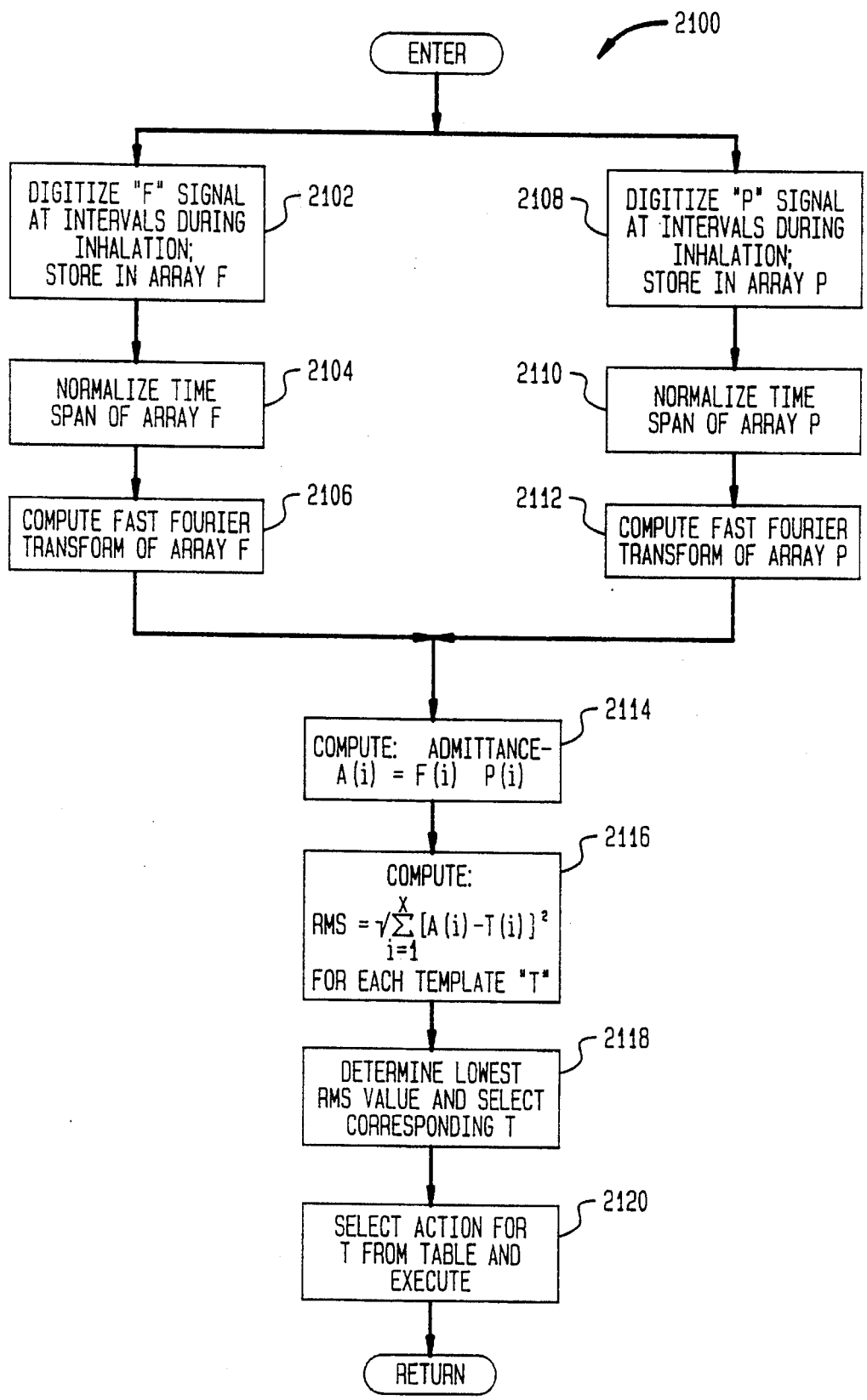

FIG. 6 presents graphical illustrations of a typical breathing cycle including an inhalation phase and an exhalation phase, of the nasal air pressure imposed on the patient's airway during the breathing cycle, and of the vent valve steps required to maintain the set point pressures;

FIG. 7 is an electrical schematic illustration of the microcontroller and associated components of the present invention;

FIG. 8 is an electrical schematic of the blower motor control;

FIG. 9 is an electrical schematic of the stepper motor control for the vent valve;

FIG. 10 is a schematic illustration of a pressure transducer circuit;

FIG. 11 is a computer program flowchart illustrating the START-UP portion of the main routine;

FIG. 12 is a computer program flowchart of the MAIN LOOP portion of the main routine;

FIG. 13 is a computer program flowchart of the VALVE STEP subroutine;

FIG. 14 is a computer program flowchart of the ADC interrupt;

FIG. 15 is a computer program flowchart of the CHECK BLOWER SPEED subroutine;

FIG. 16 is an electrical block diagram illustrating the spectral sound analysis circuit;

FIG. 17 is a computer program flowchart of the SOUND ANALYSIS subroutine;

FIG. 18 is a schematic block diagram of another embodiment of the invention for determining patient airway patency;

FIG. 19 is a set of five graphs of the embodiment of FIG. 18 illustrating airway flow, pressure and admittance, and further illustrating two admittance templates;

FIG. 20 is a computer program flowchart for operating the microcontroller of FIG. 18; and FIG. 21 is a computer program flowchart of another program embodiment for operating the microcontroller of FIG. 18.

Figure 22:
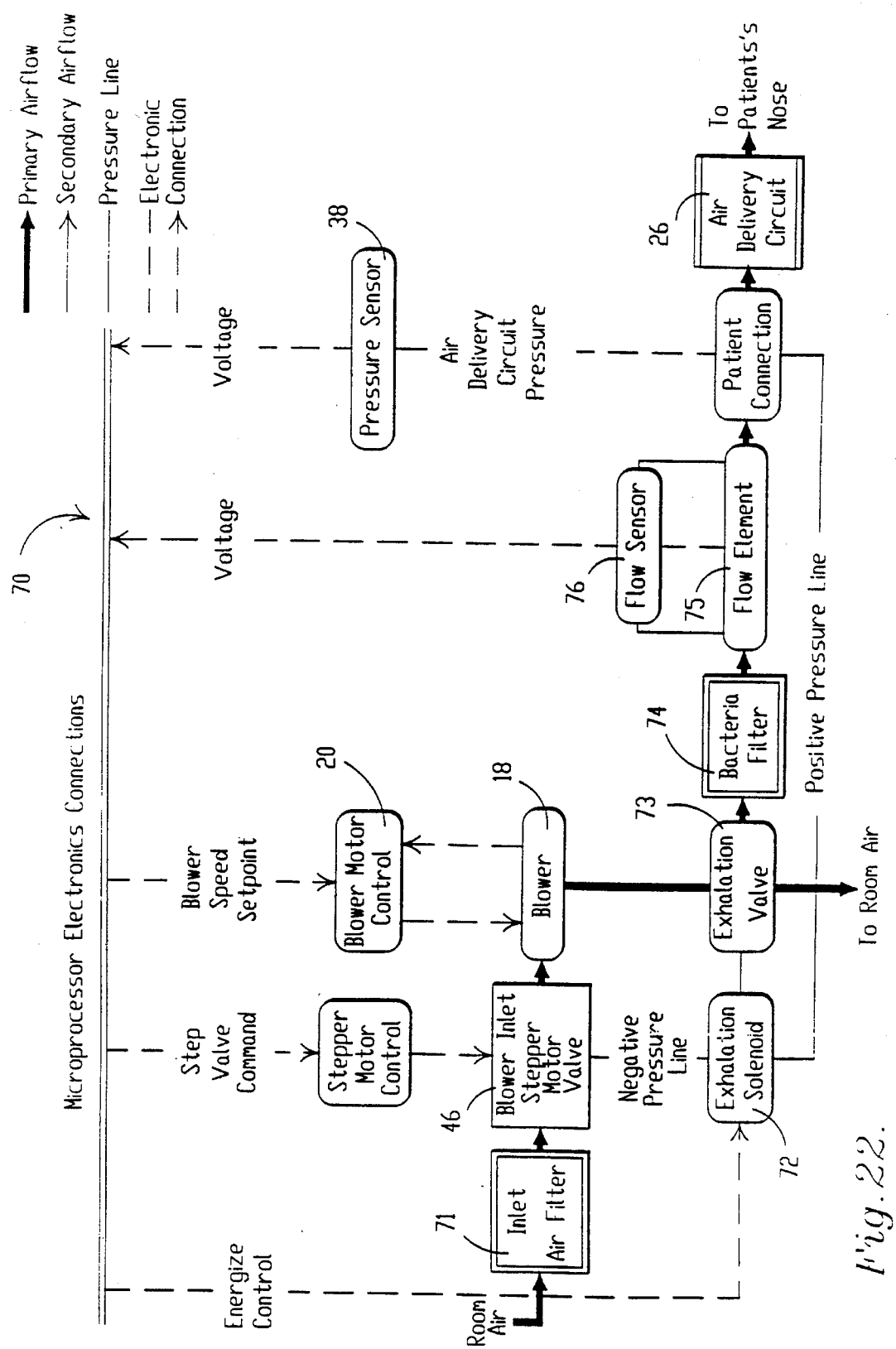
Figure 24:
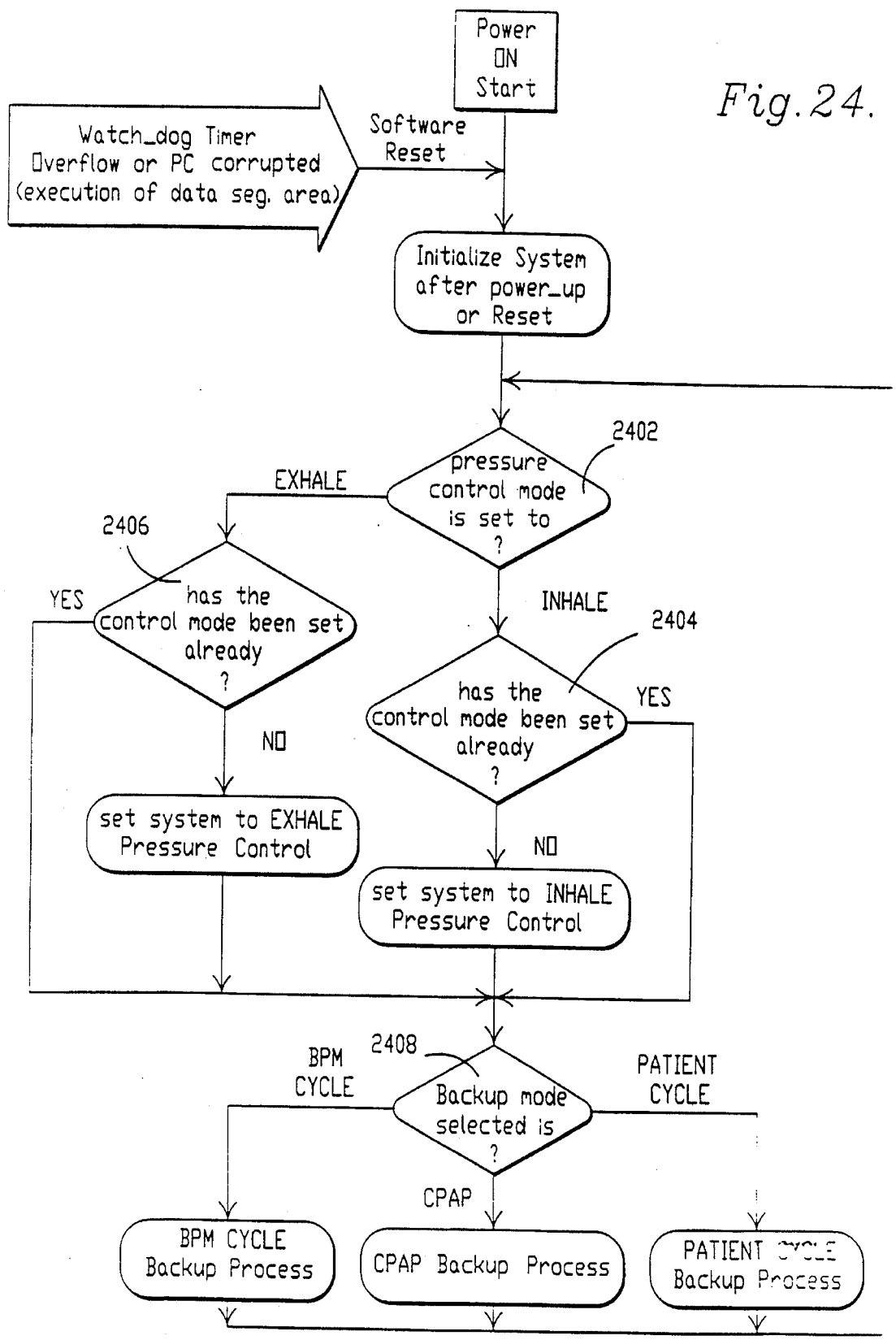
Figure 25:
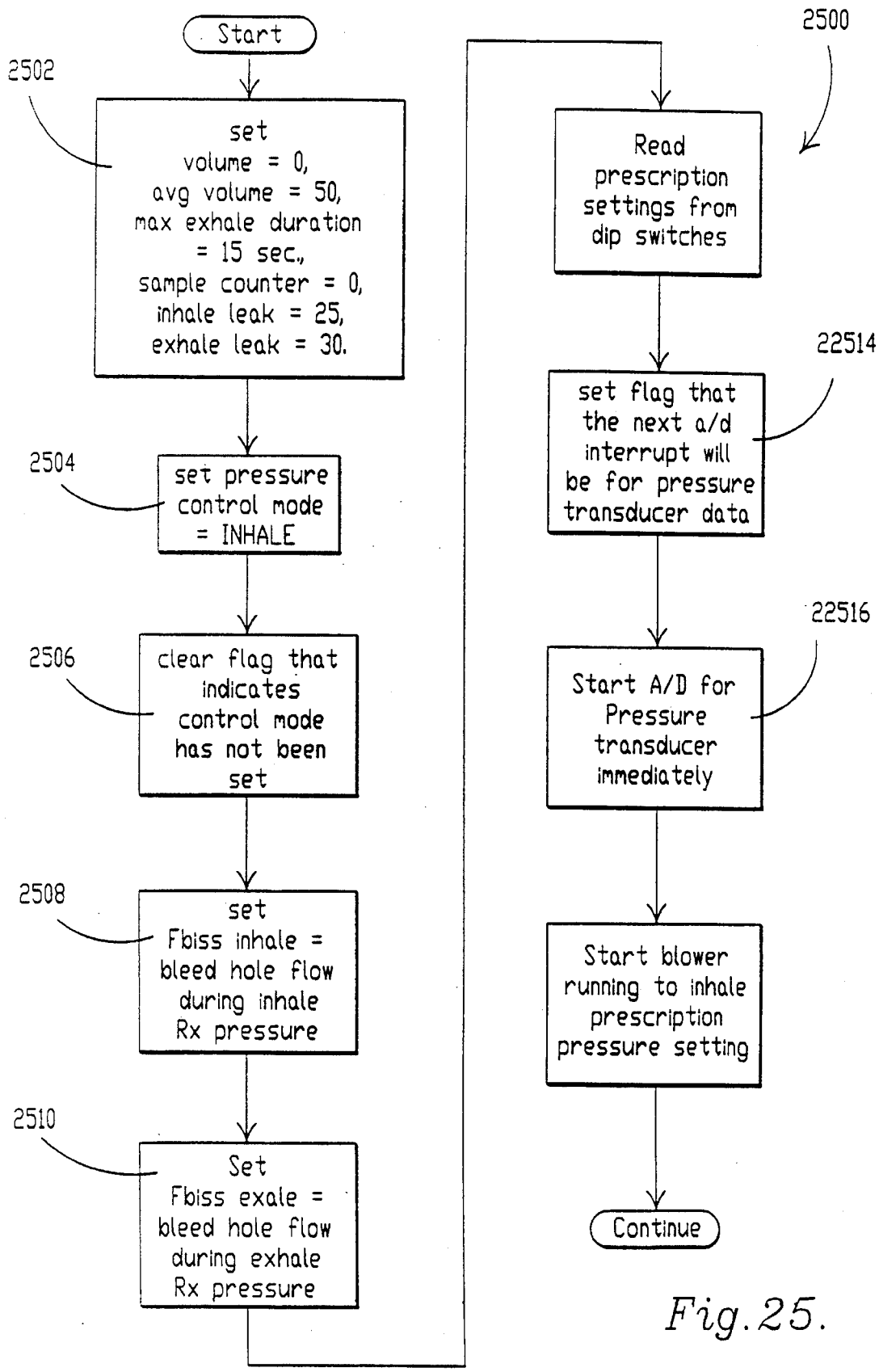
Figure 26:
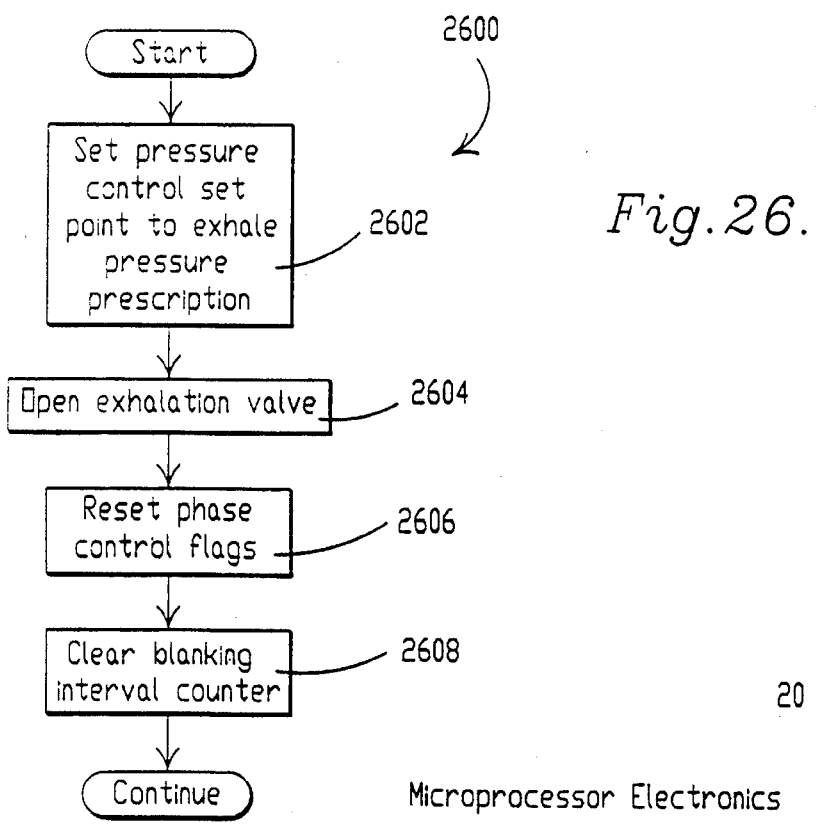
Figure 23:
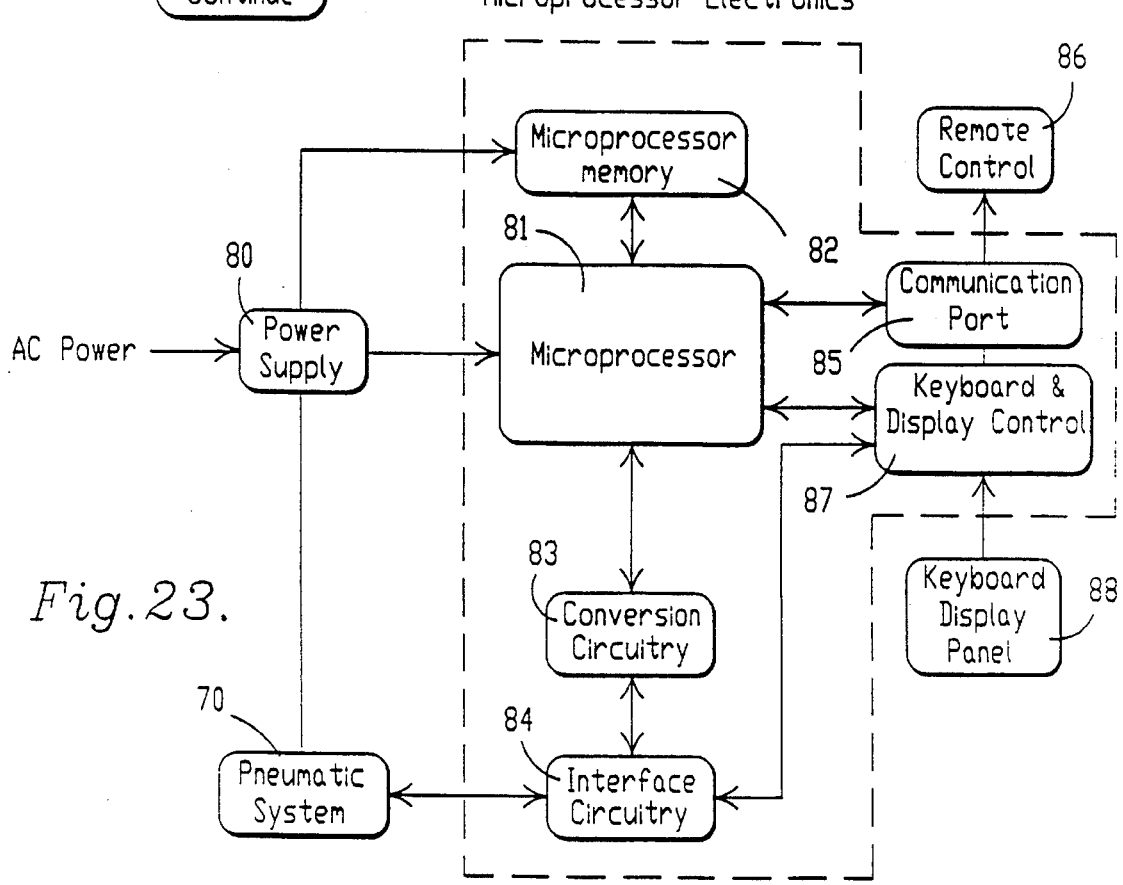
Figure 27:
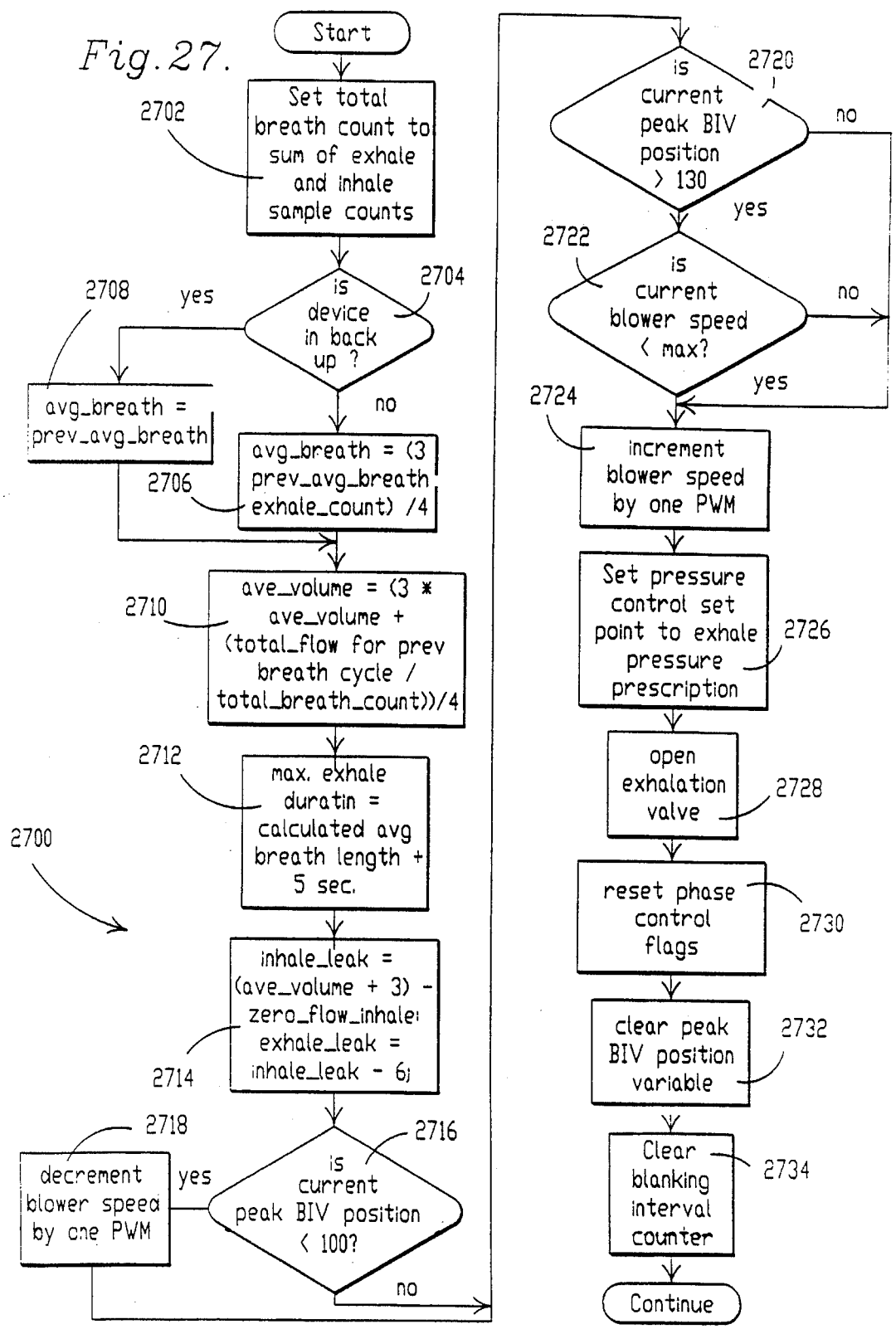
Figure 28:
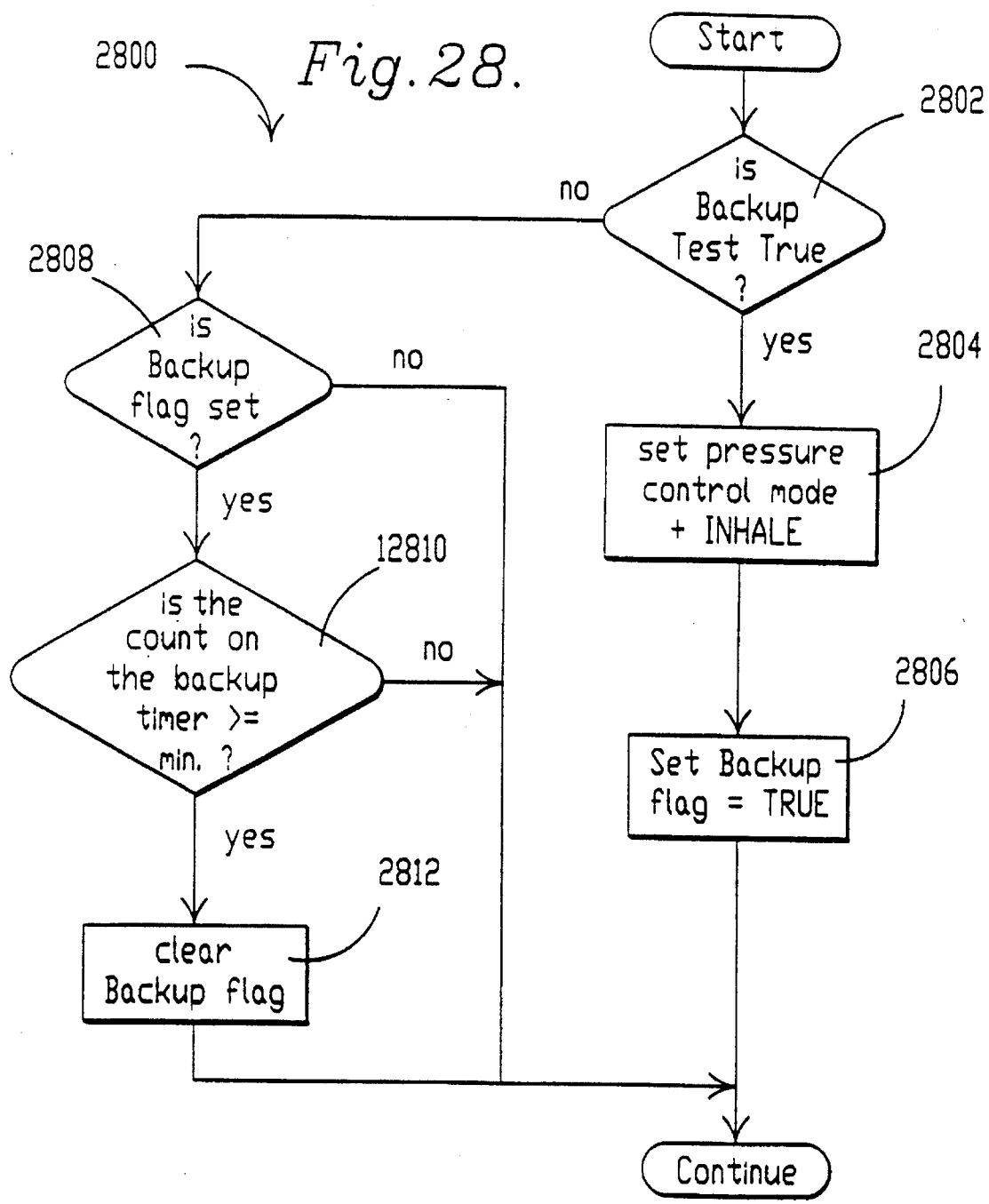
Figure 29:
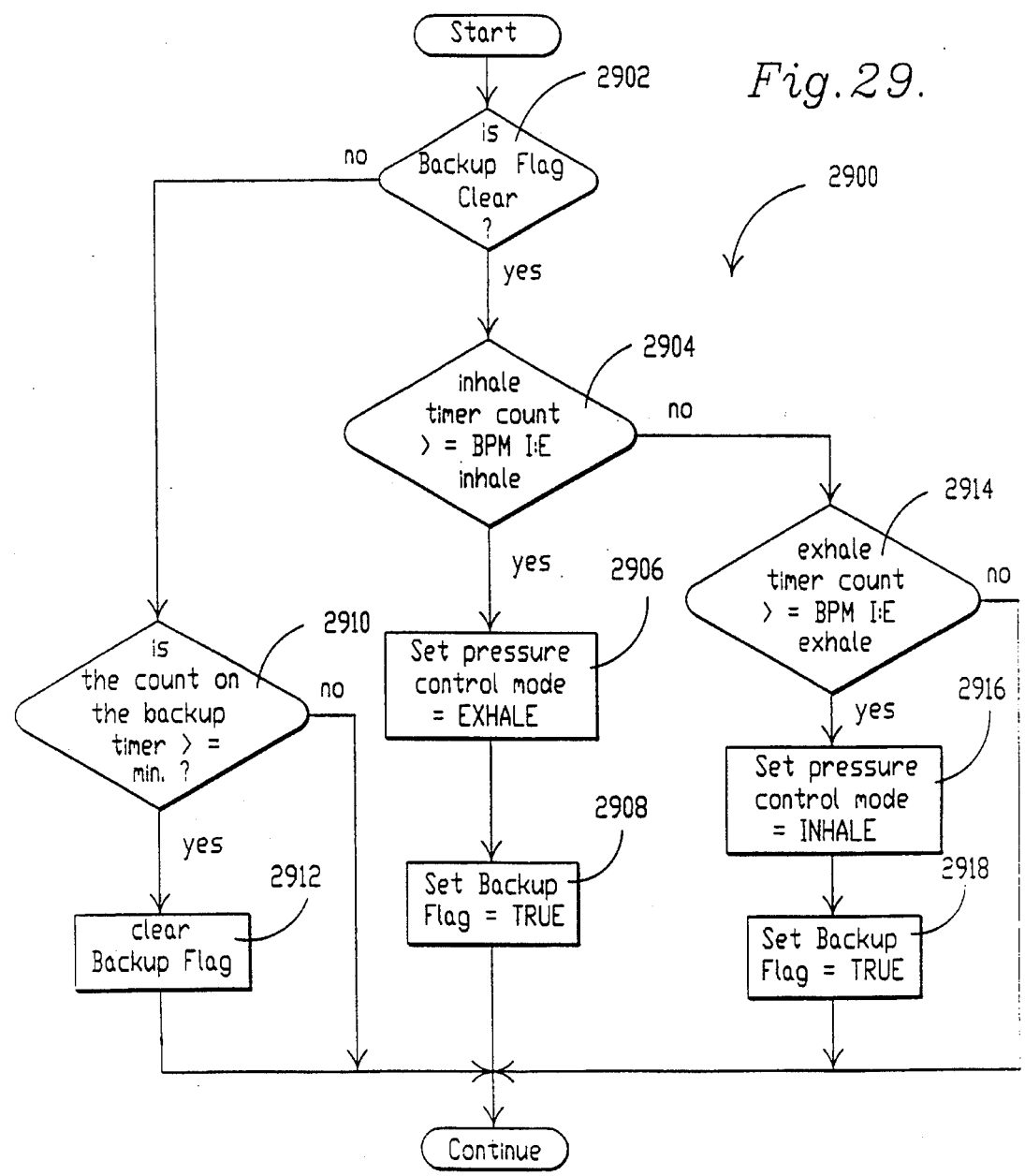
Figure 31A:
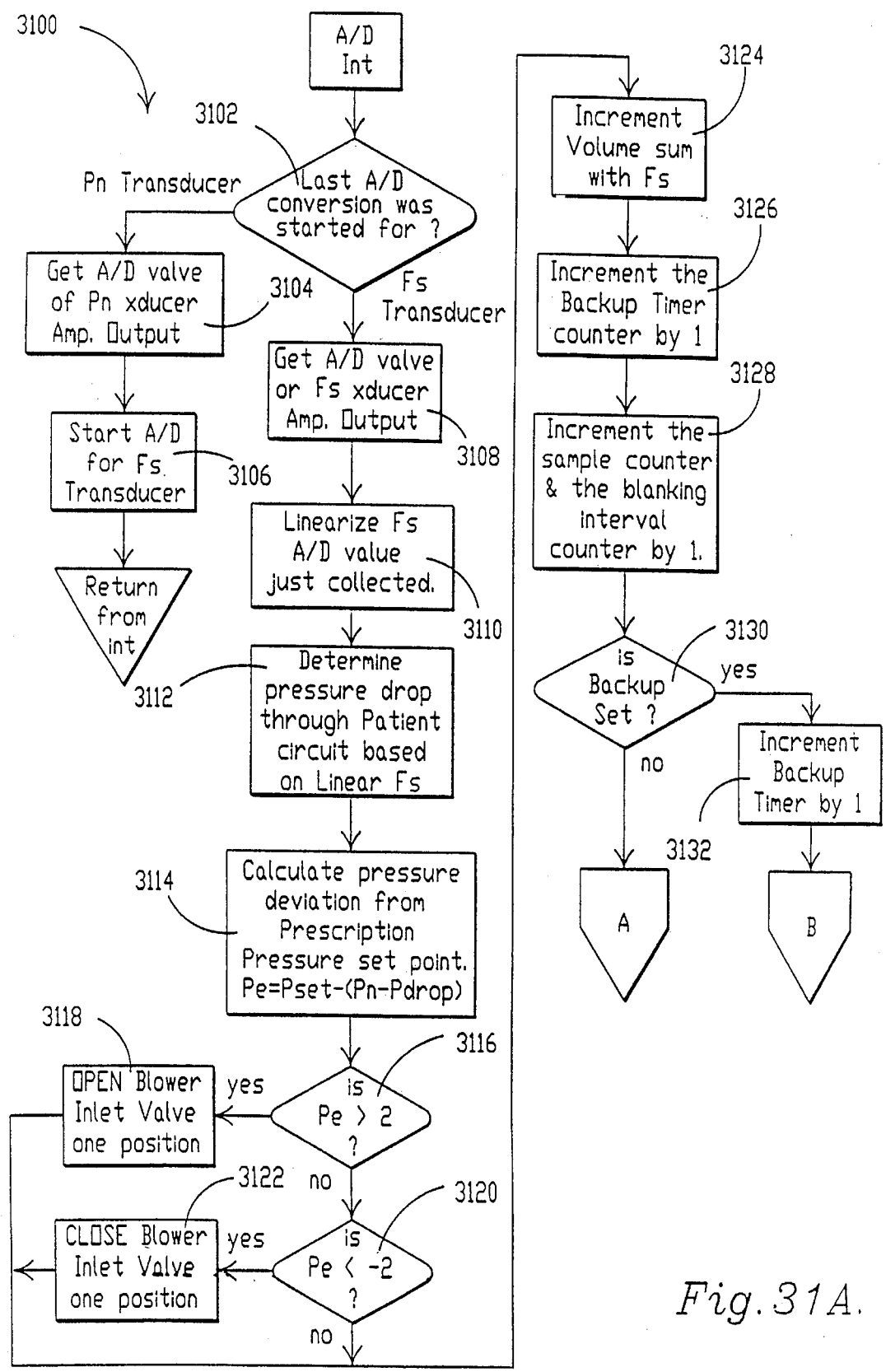
Figure 31B:
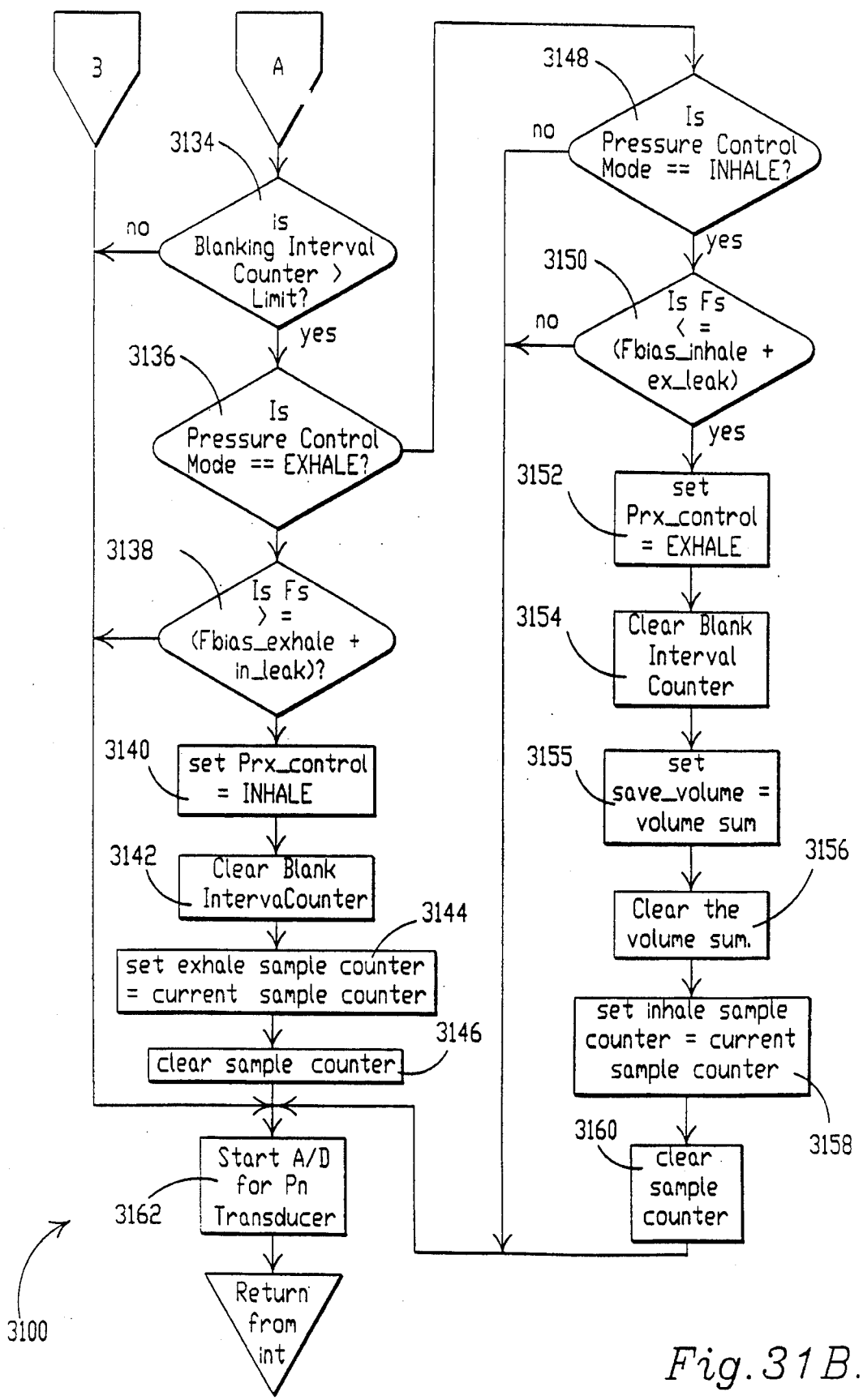

FIG. 22 is a block diagram of the pneumatic components of the compensation embodiment of the present invention;

FIG. 23 is a block diagram of the electronic components associated with the compensation embodiment of FIG. 22;

FIG. 24 is a computer program flowchart of the PRIMARY module for operating the compensation embodiment;

FIG. 25 is a computer program flowchart of the INITIALIZE module of the PRIMARY module;

FIG. 26 is a computer program flowchart of the EXHALE module of the PRIMARY module;

FIG. 27 is a computer program flowchart of the INHALE module of the PRIMARY module;

FIG. 28 is a computer program flowchart of the CPAP BACKUP module of the PRIMARY module;

FIG. 29 is a computer program flowchart of the BPM CYCLE BACKUP module of the PRIMARY module;

FIG. 30 is a computer program flowchart of the PATIENT CYCLE BACKUP module of the PRIMARY module;

FIG. 31A is a computer program flowchart of the first portion of the A/D INTERRUPT module of the PRIMARY module; and FIG. 31B is a computer program flowchart of the remaining portion of the A/D INTERRUPT module.

DETAILED DESCRIPTION OF THE PREFERRED EMBODIMENTS

With reference to the drawing figures, FIG. 3 schematically illustrates the single conduit embodiment of the preferred inspiratory airway pressure apparatus 10 which broadly includes an elongated, flexible, hose or conduit 12, nasal pillow 14 connected to one end of conduit 12, vent valve assembly 16 positioned adjacent the opposed, open, vent end of conduit 12, blower unit 18 fluidically coupled with conduit 12 between pillow 14 and vent valve assembly 16, and controller 20 which is adapted for pneumatic connection with nasal pillow 14 and electrical connection with vent valve assembly 16 and blower unit 18.

In the preferred embodiment, vent valve assembly 16, blower unit 18, and controller 20 are housed within cabinet 22 such as that illustrated in FIG. 2 in connection with the dual-conduit embodiment. In this regard, conduit 12 presents an interior portion which is housed within cabinet 22 and exterior portion 26 which extends from the cabinet to nasal pillow 14. Conduit 12 additionally presents coupling end 28 coupled to nasal pillow 14, inlet end 30 coupled with blower unit 18 for receiving a supply of breathable gas, preferably ambient air therefrom, and vent end 32 positioned adjacent vent valve assembly 16.

Nasal pillow 14 is the preferred patient-coupling device and is further illustrated in U.S. Patent No. 4,782,832 which is hereby incorporated by reference. Head gear 34 holds nasal pillow 14 on the head of patient 36 in order to fluidically couple with the respiratory passages of patient 36, and preferably with the patient's nares. Nasal pillow 14 is configured to present pressure sensor fitting 38 which is coupled with controller 20 by pneumatic line 40 which is preferably routed within conduit 12 so that line 40 is conveniently out of the way and less likely to be pinched or restricted by the patient during use of apparatus 10. Nasal pillow 14 also includes vent port 42 defined therethrough which continuously vents a small amount of pressure from nasal pillow 14 in order to prevent moisture buildup and subsequent condensation therein. Port 42 also prevents build up of exhaled gases including carbon dioxide.

Vent valve assembly 16 includes stepper motor 44 and valve element 46 connected to the output shaft thereof. Valve element 46 is preferably constructed of a flat plate configured to present two, opposed, arcuate, cam-like edges 48a,b as illustrated in FIG. 5. Element 46 is positioned adjacent vent end 32 of conduit 12 so that as stepper motor 44 rotates valve element 46 in a clockwise direction as viewed in FIG. 5, edge 48a progressively covers and thereby restricts vent end 32. Conversely, as motor 44 rotates element 46 in a counterclockwise direction, edge 48a progressively exposes an increasing area of vent end 32 to vent additionally gas therefrom.

FIG. 4 illustrates the dual-conduit second embodiment of preferred apparatus 10. This embodiment is similar to that of FIG. 3 and corresponding components are numbered the same. Second embodiment 50 additionally includes exhaust hose 52 presenting connection end 54 fluidically coupled to conduit exterior portion 26 at junction 56, and presents exhaust end 58 positioned adjacent valve element 46 in the same opening/closing relationship with arcuate edge 48b as vent end 32 presents to arcuate edge 48a. With this configuration, conduit 12 additionally presents inhalation hose 60 between juncture 56 and blower unit 18. In the dual hose model, nasal pillow 14 does not include vent hole 42, and the tube between ends 54 and 28 include divider 61 to separate it into two separate passages. Second embodiment 50 may also include inhalation check valve 62 disposed within inhalation hose 60 adjacent juncture 56, and exhalation check valve 64 disposed within exhaust hose 52 also adjacent juncture 56. Inhalation check valve 62 prevents passage of patient exhalation therethrough toward vent end 32 and thereby requires that the patient's exhalation exit the system through exhaust end 58. Pneumatic lines 66 and 68 respectively couple controller 20 with inhalation hose 60 and exhaust hose 52.

By way of overview, controller 20 controls apparatus 10 in order to increase the gas pressure presented to the patient at a time in the patient's breathing cycle just prior to inhalation, and to subsequently lower the pressure for ease of exhalation. The upper graph of FIG. 6 illustrates a typical breath cycle air flow. During inhalation, the flow rate of gas to the patient gradually increases to a maximum and then decreases. At the end of inhalation, the patient typically experiences a slight pause before exhalation begins. During exhalation, the exhaled gas flow from the patient gradually increases to a maximum and then decreases again. A post-exhalation pause, typically somewhat longer than the post-inhalation pause, follows exhalation. After the post-exhalation pause, the patient again begins inhalation.

The middle graph of FIG. 6 illustrates the nasal airway pressure presented to patient 36 during operation of apparatus 10. With patients subject to sleep apnea, it is desirable to increase nasal airway pressure just prior to inhalation to splint airway pressure in order to position the genioglossus tissue and thereby maintain the airway open. Accordingly, this middle graph illustrates an increase in the nasal airway pressure just prior to inhalation to a selected prescription pressure level sufficient to push surrounding tissue aside and open this airway. After completion of inhalation, the set point pressure presented to the nasal airway is reduced so that exhalation occurs against a low or even zero pressure level relative to ambient. At the end of exhalation, the nasal airway pressure is again increased prior to the next inhalation phase.

To accomplish these pressure variations, blower unit 18, in one embodiment of the invention, produces a generally constant volume per unit time of breathable gas which is selectively vented through vent end 32. The vented gas volume is controlled by vent valve assembly 16.

The bottom graph of FIG. 6 graphically depicts the various positions of valve element 46 in relation to vent end 32 in order to achieve the desired nasal airway pressure profile illustrated in the middle graph. For example, during the post-exhalation pause, controller 20 activates stepper motor 44 to rotate valve element 46 in a clockwise direction (as viewed in FIG. 5) in order to increase the nasal airway pressure to the desired set point as sensed by controller 20 by way of pneumatic line 40. When the patient begins to inhale, gas output from blower unit 18 is inhaled by the patient. In order to maintain the set point pressure, the controller then rotates valve element 46 in stepwise fashion further in the clockwise direction to reduce the amount of gas being vented. As inhalation passes its peak flow rate, controller 20 begins to reverse the position of valve element 46 to vent additional gas for maintaining the set point pressure.

At the end of inhalation, a lower pressure set point is desired and controller 20 continues, in stepwise fashion, to rotate valve element 46 in the counterclockwise direction to vent additional amounts of gas for achieving a new lower set point pressure.

At the end of the post-inhalation pause, the patient begins to exhale. In order to maintain desired lower set point pressure, the additionally exhausted gas from the patient must be vented through vent end 32. Accordingly, controller 20 causes valve element 46 to further rotate in a clockwise direction to open vent end 32 even further. As the exhalation flow rate decreases, controller 20 rotates valve element 46 in a clockwise direction to decrease venting in order to maintain the lower set point pressure. At the end of exhalation, controller 20 then causes valve element 46 to rotate further in the clockwise direction to increase the pressure to the higher pressure set point. This induces tension in the geniogiossus muscle to open the airway in preparation for the next inhalation phase.

Inspection of the upper and lower graphs reveals a similarity in the profile of the curves. That is to say, controller 20 is able to track a patients breathing cycle by tracking the stepped positions of valve element 46 required to maintain the set point pressures. In this way, controller 20 is able to determine the end of respective inhalation/exhalation phases and to predict exhalation and inhalation interval times.

Turning now to controller 20, it provides electrical outputs to control the speed of blower unit 18 and the position of stepper motor 44. Controller 20 receives electrical feedback from blower unit 18 indicative of the speed thereof, and a pneumatic input by way of pneumatic line 40 to indicate the pressure at nasal pillow 14 and thereby in the patient's nasal airway passages.

Controller 20 includes pressure transducer circuit 700 (FIG. 7) for providing an electrical input indicative of the pressure at nasal pillow 14 to microcontroller circuit 800 (FIG. 8) which in turn provides outputs to blower motor circuit 900 (FIG. 9) and stepper motor circuit 1000 (FIG. 10). Additionally, controller 20 includes a conventional 120 v.a.c. to +5 v.d.c., +12 v.d.c., and +24 v.d.c. power supply (not shown) suitable for digital and analog, solid state integrated circuit components.

Pressure transducer circuit 700 illustrated in FIG. 7 is typical of the pressure transducer circuit for both the single and dual conduit embodiments of the present invention. That is to say, the single conduit embodiment of FIG. 3 uses only one pressure transducer whereas the embodiment schematically illustrated in FIG. 4 uses two pressure transducers both using a circuit as illustrated in FIG. 7.

The preferred pressure transducer includes SENSYM type SX01DN having a zero-to 70-cm. water operational range. The preferred transducer includes four strain gages arranged in a conventional Wheatstone bridge 701 having strain gages X1, X2, X3, and X4 presenting a nominal 4650 ohms each. Bridge 701 presents excitation terminal 702 connected to +12 v.d.c. and an opposed excitation terminal 704 connected to ground as shown. Bridge 701 produces outputs at terminals 706 and 708. Zero adjustment potentiometer 710 interconnects terminals 704 and 706.

The output from terminal 708 is connected to the positive input terminal of operational amplifier 712 (one-half of Type LT1014). The output of operational amplifier 712 provides feedback to the negative input terminal thereof, and, by way of resistor R1 (1K ohms) supplies the positive input terminal of amplifier 714. The output is also connected to ground by way of resistor R2 (750K ohms).

Strain gage bridge output terminal 706 is connected to the positive input terminal of operational amplifier 716 (the other half of unit LT1014). The output from amplifier 716 provides feedback to the negative input terminal thereof and is connected by way of resistor R3 (1K ohms) to the negative input terminal of amplifier 714.

The output from amplifier 714 provides feedback to the negative input terminal thereof by way of resistor R4 (750K ohms). The output from amplifier 714 is also connected by way of resistor R5 to output terminal 718 which, by way of the circuitry just described, provides output between 0 and +5 v.d.c. corresponding to a pressure of 0 to 25 cm. water.

A similar output is provided at a corresponding terminal 720 if a second pressure transducer is used. In the dual-conduit embodiment, two transducers provide additional pressure information which allows more precise tracking of inhalation and exhalation gas flows of the patient, and thereby more precise breath cycle tracking.

FIG. 8 is an electrical schematic diagram of microcontroller circuit 800 which includes microcontroller 802 (intel Type 8097BH), programmable array logic (PAL) (Type PC16L8), erasable, programmable, read-only-memory (EPROM) (Type 27256), address latch 808 (Type 74HC373), random access memory (RAM) (Type 6264P), input/output serial data interlace (RS232 Type MAX232), prescription (RX) switch array 814, and input data latch 816.

Microcontroller 802 receives power (Vcc) at +5 v.d.c. at terminals VCC, VPD, BW, RDY, VPP, and VREF as shown. Ground is connected to terminals NMI, VSS, EA, and ANGND. Crystal 802 is coupled between terminals XTAL1 and XTAL2 as shown and to which respective grounded capacitors C1 and C2 (33 pF each) are respectively coupled for timing signals at 12 MHZ.

Microcontroller 802 receives a reset signal at terminal RESET from reset sub-circuit 820. On power up, power is supplied through resistor R5 (100K ohms) to grounded capacitor C3 (22 uF) and to the input terminals of SCHMITT trigger NAND gate 822. Initially, the resultant input voltage to NAND 822 is low, and its output is logic high. This logic high output is supplied to output terminal 824 which provides a reset signal to blower motor circuit 900 as discussed further hereinbelow. The initially logic high output from NAND 822 is inverted by invertor 826 to provide a logic low signal to microcontroller terminal RESET which holds microcontroller 802 in reset until the charge on capacitor C3 builds to the trigger level of NAND 822. This provides time for the system to initialize and for transients to be suppressed. As the charge on capacitor C3 increases to the trigger level, the reset signal is removed from output terminal 824 and microcontroller 802. The output from invertor 826 is also connected to one side of pull-up resistor R6 (10K ohms) the other side of which is connected to Vcc.

Reset circuit 820 also includes a normally open, reset switch 828 coupled across capacitor C3 which allows manual reset. Diode D1 is coupled access resistor R5 to provide a discharge path for C5 in the event of power off.

Microcontroller 802 also receives a pressure transducer input at terminal ACH0 and also at ACH1 if a second transducer is used as in the dual-conduit embodiment. To provide transient suppression, and to smooth the analog voltage from pressure transducer circuit 700, one side of capacitor C4 (0.005 nF) is connected to terminal 718 along with the anode of diode D2 and the cathode of diode D3. The other side of capacitor C4 and the anode of diode D3 are connected to ground as shown and the cathode of diode D2 is connected to a supply voltage Vcc. An identical circuit is provided for terminal 720 using diodes D4, D5 and capacitor C5. Microcontroller 802 includes internal analog-to-digital converters (ADC) which receive the respective analog inputs at terminals ACH0 and ACH1 and convert these to digital form for internal use in microcontroller 802.

Microcontroller 802 also receives an input at terminal HS1.0 which is a pulse signal from blower motor circuit 900 representative of the speed of blower unit 18, discussed further hereinbelow.

Microcontroller 802 also uses a common address/data bus 830 which interconnects microcontroller 802 for data and address information flow with PAL 804., EPROM 806, address latch 808, RAM 810, and data latch 816 at the terminals as shown in FIG. 8. FIG. 8 also illustrates the other conventional interconnections between these components as shown.

Microcontroller 802 provides a serial data output from terminal TXD to terminal 11 of interface 812 and receives data from terminal 12 thereof at microcontroller terminal RXD. Interface terminals 14 and 13 receive RS232 data in and out which enable remote reading and control of microcontroller 802 and thereby apparatus 10. This feature is particularly useful in a sleep taboratory, for example, for adjusting the prescription pressures in order to achieve the optimal therapy.

Switch array 814 includes eight, selectable switches for providing input data representative of the desired prescription set point pressures for inhalation and exhalation. In particular, the top four switches are used to set the prescription inhalation pressure and the bottom four switches for prescription exhalation pressure. With four switches for each set point, sixteen possible settings are available ranging between 3 and 16 cm water for inhalation, and 0 and 14 cm water for exhalation. Data latch 816 is coupled with switch array 814 as shown and latches the prescription data upon receipt of the latch signal from terminal 12 of PAL 804. The prescription data is transmitted over bus 830.

Microcontroller 802 also provides two additional outputs. The first of these is data to stepper motor circuit 1000 by way of six-line output bus 832 from microcontroller terminals P1.0–1.5 to output terminal 834. The second additional output is a pulse-width modulated signal (PWM) to blower motor circuit 900 by way of line 834 and output terminal 836.

FIG. 9 is an electrical schematic diagram representing blower motor circuit 900 which receives the pulse width modulated signal at terminal 836 from microcontroller 802, and also receives an inverted reset signal at terminal 824 from reset circuit 820. Blower motor circuit 900 also provides a pulse output signal at terminal 902 representative of the speed of blower motor 904 to microcontroller 802.

The reset signal received at terminal 824 is connected to terminal 10 of motor driver 906 (Type UC3524A). The pulse width modulated signal from controller 802 at terminal 836 is provided to terminal 2 of driver 906 by way of low pass filter C6 (1.0 uF) and resister R7 (24.9K ohms).

Driver terminal 7 is connected to ground by way of capacitor C7 (0.003 uF), and terminal 6 is connected to ground by way of resistor R8 (49.9K ohms). Terminal 8 is connected to ground and terminal 15 receives power supply at +12 v.d.c. Driver terminal 12, 13, and 16 are connected to Vcc at +5 v.d.c.

Motor driver 906 converts the input pulse-width modulated signal at 0–5 v.d.c. to a corresponding output at 0 to +12 v.d.c. at terminals 11 and 14 thereof to programmable array logic (PAL) (Type 16L8) terminal 1. These terminals are also connected to ground by way of resistor R9 (0.5 ohms). PAL 908 produces respective outputs at terminals 19 and 18 as two phases for the stator and rotor of brushless D.C. blower motor 904 (Fasco Corp. Type 70000-S517). The PAL 908 outputs are respective inputs to level converters 910 and 912 (MC14504) which shift the voltage level from +5 to +12 v.d.c. The +12 v.d.c. outputs from level converters 910 and 912 are in turn transmitted to the respective gates of field effect transistors (SENSFET) (Motorola SENSFET Type MTP40N06M) 914 and 916. The respective drain terminals of SENSFETS 914 and 916 are respectively connected to terminals 0A and 0B of blower motor 904 and provide the respective phase inputs to the stator and rotor thereof.

Power at +12 v.d.c. is additionally provided to level converters 910 and 912 and to common power terminal CP of blower motor 904.

The source terminal of each SENSFET 914, 916 is connected to ground as shown.

SENSFETS 914,916 each include an additional pair of outputs on lines 918 and 920 which provide a sampling of the current flow through the respective SENSFETS. These outputs are coupled across resistor R10 (100 ohms) to provide a current path for the current sample, and thereby a voltage representative thereof to terminals 3 and 4 of motor driver 906. Driver 906 is responsive to this input voltage representative of the current flow through blower motor 904 to reduce the duty cycle of the output at terminals 11 and 14 in the event of motor overcurrent.

Blower motor 904 is additionally equipped with Hall effect transducer which is operable to provide a voltage pulse each time a magnetic pole of the motor stator passes thereby. These output pulses represent the speed of motor 904 and are provided at motor terminal HALL by way of line 922 to output terminal 902, and as feedback to motor driver 906. The output pulses representative of motor blower speed at terminal 902 are provided to microcontroller 802 at terminal HS1.0 thereof.

The pulses representative of motor blower speed are converted to a representative voltage before input to motor driver terminals 1 and 9. As shown in FIG. 9, line 922 is connected to one side of capacitor C8 (0.01 uF) the other side of which is connected to one side of resistor R11 (10 K ohms), and to the anode of diode D6. The other side of resistor R 11 is connected to ground.

The cathode of diode D6 is connected to one side of grounded capacitor C9 (0.1 uF), to grounded resistor R12 (1M ohms) and to one side of resistor R13 (100K ohms). The other side of resistor R13 is connected to one side of capacitor C10 (0.22 uF), to one side of resistor R14 (10M ohms), and to motor driver terminal 1 as input thereto. The other side of capacitor C10 and resistor R14 are connected to driver terminal 9.

This network of components C8–C10, R11–R14, and diode D6 convert the frequency pulses on line 922 to a voltage representative thereof. That is to say, this network acts as a frequency-to-voltage converter owing to the large capacitance of capacitor C9 (0.1 uF) which provides a long time constant. The voltage value provided at motor driver terminals 1 and 9 provides feedback to an internal comparator which compares the voltage to a set point derived from the pulse width modulated signal received at terminal 2.

FIG. 10 illustrates stepper motor circuit 1000 which activates stepper motor 44 to position valve element 46 in accordance with data received from microcontroller 802 at terminal 834 therefrom. Stepper motor 44 is preferably a VEXTA model available from Oriental Motor Company and is capable of providing one revolution in 400 "steps" and is also capable of half-stepping if needed. As those skilled in the art will appreciate, motor 44 is operable to shift one step upon the imposition of the next sequential voltage step pattern provided as input at terminal 834 over output bus 832. In particular, bus 832 includes six lines, which are pattern data for the driver chip.

The step pattern data is provided to step motor driver chip 1002 (Type S'GS' L298N) at terminals A, B, C, and D respectively from terminals P1.0–1.3 of microcontroller 802. Driver 1002 shifts the input data voltage from +5 v.d.c. to +12 v.d.c. for corresponding output at terminals 2, 3, 13, and 14 which are connected to stepper motor 44 to impose the step pattern thereon at +12 v.d.c. The anodes of diodes D7, 8, 9, and 10 are connected to the respective four output lines of driver 1002, and the cathodes thereof are connected to +12 v.d.c. for voltage pull-up. Correspondingly, the cathodes of diodes D 11, 12, 13, and 14 are connected respectively to the output lines, and the respective diode cathodes connected to ground as shown for voltage pull-down.

As shown in FIG. 10, +5 v.d.c. is provided at driver terminal 9, +12 v.d.c. at driver terminal 4, and terminals 1, 8, and 15 are all connected to ground.

FIGS. 11–14 are computer program flowcharts illustrating the operative program for microcontroller 802.

FIG. 11 illustrates the START-UP portion of the main routine of the computer program for operating microcontroller 802. After the logic low reset signal goes logic high, the program enters at step 1102 which prompts controller 20 to shift vent valve assembly 16 to its "home" position. In particular, this step prompts microcontroller 802 to produce data of sequential pattern outputs by way of line 832 and terminal 834 to stepper motor control circuit 1000. This shifts stepper motor 44 to a mid-range position wherein valve element 46 blocks conduit ends 32 and 58 about half-way as shown in FIG. 5, or conduit end 32 alone in the single conduit embodiment. Step 1102 also initializes the variables, counters, interrupt routines, and so forth in the program.

The program then moves to step 1104 to read the inhalation and exhalation prescription pressure values as set on switch array 814 and read by way of address data bus 830. These values are then stored in RAM. Step 1104 also prompts microcontroller 802 to set the operating speed of blower motor 904 in accordance with the prescription of pressure set on switch 814. The blower speed should be set at a level fast enough to ensure that sufficient ambient air volume is provided to conduit 12 such that the prescription pressure level can be attained during maximum inhalation. Blower motor speed data corresponding to prescription settings are stored preferably in a look-up table. Step 1104 also clears any value stored in the internal buffer at microcontroller terminal HS1.0.

The program then moves to step 1106 which enables the program's timed interrupts to begin timing.

In step 1108 the program sets the software flag "phase" equal to inhalation "I" which initializes the program from the inhalation phase of the patient's breathing cycle. This step also initializes the blower check counter at zero. As discussed further hereinbelow, the program reads the blower speed after 128 passes through the main loop.

The program then moves to step 1110 which stars the internal analog-to-digital converter (ADC) connected to microcontroller input terminals ACH0 and ACH1.

Step 1112 sets the pressure set point for the inhalation phase according to the inhalation prescription value set on switch array 814 according to data in a look-up table. This step also defines the start-up mode of the apparatus as continuous positive airway pressure (CPAP). That is to say, and as explained further hereinbelow, the program operates apparatus 10 in order to present a continuous positive pressure at the inhalation set point pressure for the first eight breaths of a patient. Step 1112 also initializes the breath counter at zero in preparation for counting-patient breathing cycles.

After completion of step 1112 the program moves to MAIN LOOP 1200 of the main routine as illustrated in FIG. 12. Step 1202 is the first step of this routine in which the program calculates the average pressure as sensed by pressure transducer 701 over eight ADC conversions. That is to say, microcontroller 802 includes an internal "ring" buffer which stores the eight most recent pressure readings received at microcontroller terminal ACH0 (and also ACH1 in the two-conduit embodiment). As discussed further hereinbelow, ADC interrupt routine converts the input analog values to digital form every 22 microseconds and continuously stores the most recent digital values in the ring buffer. Step 1020 calculates the average value by dividing the cumulative buffer value by eight. Step 1202 also calculates the deviation, that is, error, in the average pressure from the pressure set point.

The program then moves to step 1204 which asks whether the magnitude of the error calculated in step 1202 is greater than allowed maximum error. This provides a so-called "dead band" to prevent the system from "hunting".

If the answer in step 1204 is yes, the program moves to step 1206 and calculates the number of steps and direction of stepper motor 44 required to correct the pressure deviation error. That is to say, depending upon the volume of air being produced by the blower, the fluid capacity of the system, and the leakage therefrom, the number of required steps can be determined approximately by reference to data previously stored in a look-up table.

The program then moves to step 1208 to execute routine "VALVE STEP" illustrated in FIG. 13 and discussed further hereinbelow. VALVE STEP routine 1300 sequentially presents the data patterns required to step the valve for the required number of steps in the direction determined in step 1206.

After execution of sub-routine 1300 or after step 1204, the program returns to step 1210. This step stores the number of valve steps and direction actually implemented in an internal valve slope buffer which continuously stores the previous eight movements of stepper motor 44. With this information, the slope of valve movement can be calculated by dividing the valve slope buffer sum by eight. This represents a slope because the eight values are stored at equal time intervals and thus the buffer sum divided by eight represents the first derivative of value movement.

For example, and referring to FIG. 6, after the post-exhalation pause, and after achieving the desired set point pressure, no significant error in pressure versus set point exists. Thus, no change in the value position is required and so the previous eight value steps would equal zero, indicating a slope of zero, which is indicated by the flat portion of the valve position curve in FIG. 6. In contrast, when the patient begins to inhale, the valve position must initially and quickly shift toward the closed position to maintain the pressure in conduit 32. With a number of positive steps executed on stepper motor 44, the values stored in the slope buffer indicate a high positive slope. Conversely, near the end of inhalation, the valve must execute a number of steps in the negative direction in order to maintain the pressure in conduit 32 indicating a large negative slope. This slope information, as is discussed further hereinbelow, is used to determine various points in the breathing cycle of a patient.

The program then moves to step 1212 which asks whether the phase flag is set for exhalation. The program was initialized with the phase flag set for inhalation, and so, during the first few passes through main loop 1200, the answer in 1212 is no and the program moves to step 1214 which asks whether the phase flag is set for inhalation. Because this flag is initialized as inhalation, the answer in step 1214 is yes and the program moves to step 1216.

Step 1216 asks whether the variable "timer counter" .is greater than the value for variable "inhalation end time", and whether the slope as calculated in step 1210 is less than or equal to −5. The variable "timer counter" (TMR CNT) is a software counter which was initialized at zero and increments every 13 milliseconds. The variable "inhalation end time" was initialized at a default value representing inhalation time equivalent to a predetermined average value. As discussed further hereinbelow, the variable "inhalation end time" is recalculated for each breath cycle after an initial eight passes through main loop 1200. Step 1216 operates to determine whether sufficient time has passed for normal inhalation to be complete as additionally confirmed by the value slope being less than −5 as illustrated by the slope of the value position curve at the end of inhalation in FIG. 6.

During the first few passes through main loop 1200, the answer in step 1216 is no and the program moves to step 1218 which asks whether the blower check counter, initialized at zero, is equal to 128. Until then, the answer in step 1218 is no and the program moves to step 1220 to increment the blower check counter. The program then loops back to step 1202 and repetitively executes steps 1202–1220 until the answer in step 1218 is yes whereupon the program moves to step 1222 to execute the sub-routine "CHECK BLOWER SPEED" 1200 as illustrated in FIG. 15. As discussed further hereinbelow, this step monitors the blower speed to ensure that it is running at the set point speed initially set in step 1104 in accordance with prescription settings. The program then returns to step 1224 to reset the blower check counter at zero.

After sufficient time has elapsed to exceed the default time set for the inhalation end time, and when the slope of the valve position curve is equal to or less than −5 indicating the end of patient inhalation, the answer in step 1216 is yes and the program moves to step 1218 which asks whether the mode of operation is set for inspiratory nasal air pressure (INAP). This was initialized in the CPAP mode in step 1112. During the first eight breathing cycle, the answer in step 1226 is no, and the program moves to step 1228 which asks whether the breath counter is less than or equal to eight. The breath counter was initialized at zero and during the first pass of the program the answer in step 1220 is yes, and the program moves to step 1230 to increment the breath counter.

The program then moves to step 1232 which sets the variable "cycle time" equal to the current value existing on the timer counter. This step is entered at the end of each inhalation phase and marks the end of one breath cycle and the beginning of another. Thus, the time of one breath cycle, that is, cycle time, equals the time value existing on the timer counter which is reset to zero at the end of each breath cycle, also in step 1232.

Step 1232 also sets a new inhalation interval time equal to the new cycle time divided by three. Statistically, inhalation time averages about 40% of a typical breathing cycle. Step 1232, however, sets the inhalation interval equal to 33% of the most recent cycle time in order to ensure that this value clocks out in step 1216 early, that is, before the end of anticipated actual inhalation time.

Step 1232 also sets the variable "inhalation start time" equal to the new cycle time divided by two. With the beginning of a cycle marked as the end of an inhalation phase, the next inhalation start time would normally be expected to occur after 60% of the cycle time has elapsed. Step 1232, however, sets inhalation start time at 50%, that is earlier than the predicted inhalation time in order to ensure an increase in nasal pressure before inhalation would be expected to begin.

After main loop 1200 has detected eight breath cycles as indicated on the breath counter, the answer in step 1228 is no and the program moves to step 1234 which sets the operating mode as INAP. The eight cycle delay in setting the INAP mode ensures reliable data in tracking the breath cycle.

With the mode now set as INAP, the answer during the next pass at step 1226 is yes and the program moves to step 1236 to set the pressure set point equal to the exhaust prescription. That is to say, an inhalation phase has ended as determined in step 1216, eight breaths have been tracked as determined in step 1228, the mode is set as INAP which allows a decrease in pressure during exhalation. With these conditions satisfied, the controlled pressure set point is lowered to the prescribed exhaust prescription set point.

Normally, the exhaust pressure would be prescribed a zero, that is ambient, so that the patient can exhale normally. In some circumstances, however, the therapist may desire a slight positive pressure during exhalation which is set on the lower four switches of switch array 814 (FIG. 8).

Step 1236 also sets the phase flag for exhalation.

During the next pass through main loop 1200, the answer in step 1212 is now yes, that is, the phase is "exhalation", and the program moves to step 1238 which asks whether the current value on the timer counter is greater than or equal to the inhalation start time as previously set in step 1232. In the alternative, step 1238 asks whether the valve position slope is greater than seven which independently indicates the end of exhalation. With reference to FIG. 6, at the end of exhalation, the valve must step in the positive direction rapidly in order to restrict vent end 32 for maintaining the set point pressure. This rapid change indicates a positive slope greater than 70.

If the answer in step 1238 is no, the program continues to loop through until the answer is yes at which time the program moves to step 1240 to set the phase flag for inhalation, to set the pressure set point at the inhalation prescription value, and to set the value for the variable "inhalation end time" equal to the currently existing timer count plus the inhalation interval time. The existing value of the timer counter corresponds to the time elapsed since the beginning of the current breath cycle, which marked the end of the previous inhalation phase. The inhalation phase about to begin should end on or after the current timer count value plus the inhalation interval time. Thus, step 1240 provides a new value for inhalation interval time for use in step 1216. Normally, this value is reached before the end of the actual inhalation and is used to ensure that a transient slope reading does not erroneously mark the end of the inhalation phase. Thus the requirement in step 1216 for both the expiration of the inhalation end time and a slope less than or equal to −5.

As those skilled in the art will appreciate, step 1238, in cooperation with the balance of the operating program, ensures that the inhalation set point pressure increases before the onset of patient inhalation. First, by monitoring whether the valve position slope exceeds seven, the end of exhalation can be detected. Marking the end of an exhalation phase ensures that this is a point in the breath cycle prior to the beginning of the next inhalation phase. Additionally, an increase in the pressure prior to inhalation is assured by monitoring whether the timer counter is greater than or equal to the predicted inhalation start time in step 1238. Thus, if a sporadic or erroneous slope reading were determined, an increase in nasal pressure would still be ensured prior to inhalation when the timer counter excess the predicted inhalation start time, recalling that the inhalation start time was set in step 1232 somewhat shorter than the expected start time.

FIG. 13 illustrates VALVE STEP sub-routine 1300 which operates to impose sequentially the required step patterns on stepper motor 44 by way of stepper motor circuit 1000. Sub-routine 1300 enters at step 1302 by setting the variable "final valve position" equal to the current valve position plus (or minus) the valve correction required as determined in step 1206 (FIG. 2). Step 1302 also sets the variable "valve position" equal to the current valve position.

The program then moves to step 1304 which asks whether the correction direction is greater than zero, that is, in a positive direction to restrict vent end 32, or in the opposite direction. If the answer in step 1304 is yes, the program moves to step 1306 which asks whether the final position as determined in step 1302 exceeds step 160. That is to say, this step determines whether the requested or desired final valve position is beyond the maximum allowed position. If yes, the program moves to step 1308 which sets the final valve position equal to 160.

If the answer in step 1306 is no, or after step 1308, the program moves to step 1310 to set the variable "valve position" equal to "valve position" plus one. In other words, the program increments stepper motor 44 one step at a time until the final position is achieved.

The program then moves to step 1312 which asks whether the new valve position is less than or equal to the final valve position as determined in step 1302. If no, which indicates that the desired final valve position has been achieved, the program returns to main loop step 1210.

If the answer in step 1312 is yes, indicating that the final valve position has not yet been achieved the program moves to step 1314 which retrieves the step pattern for the next blower motor step from memory. The program then activates the lines of bus 832 in order to send this step pattern to stepper motor circuit 1000 and thereby to stepper motor 34.

The program then loops back to step 1310 to continue executing step patterns one at a time in sequence until the final position is obtained.

If the rotational direction for correction requires is negative as determined in step 1304, the program moves to steps 1316–1324 as illustrated to execute the required number of stepping patterns to shift the valve in the "negative" direction to reduce pressure by venting more air. Step 1316 asks whether the final position determined in step 1302 is less than zero indicating a valve position beyond the allowable limits of travel. If yes, the program sets the final position equal to zero in step 1318.

Step 1320 then decrements the "valve position" variable and step 1322 asks whether the newly determined "valve position" is greater than or equal to the final position desired. If yes, the step moves to program 1324 and then loops back to step 1322. If the answer is step 1322 is no, the program returns to main loop step 1210.

FIG. 14 illustrates ADC interrupt sub-routine 1400 which has its interrupt executed every 14 micro-seconds for providing an analog-to-digital conversion for the pressure data received from pressure transducer circuit 700, and to store this data in memory. Subroutine 1400 enters at step 1402 which retrieves the current data from the ADC register internal to microcontroller 802. This data is then stored in the ADC buffer for use in step 1202 (FIG. 12) of the main loop. This data is stored at location "L" which is one of the eight buffer locations. The program then moves to step 1404 to increment location variable "L" so that the next set of ADC data is placed in the next buffer location. The program then moves to step 1406 which asks whether "L" is equal to eight which is greater than the number of locations provided in the ADC buffer. If yes, the program resets "L" at location zero which is the first location in the buffer. After step 1408, or if the answer in step 1406 is no, the program moves to step 1410 which instructs the ADC to begin another data conversion. The program then returns from the interrupt to the main loop.

FIG. 15 illustrates CHECK BLOWER SPEED subroutine 1500 which is entered from step 1222 of main loop 1200, and enters at step 1502 which reads the current blower speed as received at microcontroller terminal HS1.0 from the Hall effect transducer in blower motor 94. The program then moves to step 1504 which retrieves the blower speed set point corresponding to the prescription inhalation pressure and compares the set point to the sensed lower speed. The program then moves to step 1506 which asks whether the blower speed is within a maximum error range of the set point speed. If no, the program adjusts, in step 1508, the pulse-width of the pulse width modulated signal produced at microcontroller terminal PWM and transmitted to blower motor circuit 900. After step 1508, or if the answer in step 1506 is yes, the program returns to the main loop.

Airway Sounds Embodiment

FIGS. 16 and 17 illustrate another aspect of the invention in which patient airway pressure variations and, in particular, airway sounds are monitored and the patient airway pressure controlled in response. In particular, FIG. 16 is an electrical block diagram illustrating sound analysis circuit 1600 which receives input from pressure sensor circuit 700 by way of terminal 718 thereof, and which delivers outputs to microcontroller 802. As those skilled in the an will appreciate, sounds are pressure variations and as such, preferred pressure sensor circuit 700 is also operable for sensing pressure variations representative of airway sounds and in convening these variations into representative signals at terminal 718.

The signals from pressure sensor circuit 700 are delivered to preamplifier 1602 which boosts the signal level for delivery to low-pass filter 1604, band-pass filter 1606, band-pass filter 1608, and high pass filter 1610. Low-pass filter 1604 is included to provide output "DC" to microcontroller 802 indicative of low frequency (subaudio) pressure variations and nasal pressure.

Filters 1606-10 split the audio frequency spectrum into three components: 10–200 Hz., 200–800 Hz., and 800+ Hz. respectively. The outputs from filters 1606–10 pass through respective rectifiers 1612, 1614, and 1616 which in turn provide rectified outputs to low-pass filters 1618, 1620, and 1622. Low-pass filters 1618–22 convert the respective rectified inputs to equivalent D.C. voltage outputs "LOW", "MED", and "HI" which represent the respective audio spectral components. These three outputs along with output "DC" are provided as inputs to microcontroller 802 which uses internal analog-to-digital conversion to produce digital data representative of the three spectrum components.

FIG. 17 is a computer program flowchart of SOUND ANALYSIS subroutine 1700 which is advantageously included as pan of the program for operating the microcontroller 802 in connection with the pressure variation aspect of the invention. Subroutine 1700 enters at step 1702 which initiates analog-to-digital conversion of the analog inputs "DC", "LOW", "MED", "HI" received from circuit 1600. In the preferred embodiment, step 1702 is implemented a number of times (for example, ten times) for each inhalation and the conversion values averaged. The average values of the digital representations of DC, LOW, MED and HI are then used for steps 1706–1716 as discussed further hereinbelow.

The program then moves to step 1704 which sets the software variable "old state" (OS) equal to the variable "new state" (NS) determined in the previous passes through the program. This step then sets variable NS equal to zero.

In step 1706 the program asks whether input "DC" is greater than a predetermined threshold value. This threshold value is set at a level sufficient to indicate that detectable airway sounds are occurring. If the answer is no, the program returns to the main loop. If yes, the program moves to 1708 in which, along with subsequent steps, conducts a spectral analysis of the airway sounds as determined by circuit 1600. In particular, step 1708 asks whether input LOW is of a predetermined threshold. If yes, the program moves to step 1710 which increments variable NS by 1.

If the answer in 1710 is no, or after step 1710, the program moves to step 1712 which asks whether input MED is above its associated threshold. If yes, the program moves to step 1714 which increments variable NS by 2.

If the answer in step 1712 is no, or after step 1714, the program moves to step 1716 which asks whether input HI is greater than its predetermined threshold. If yes, then step 1718 increments variable NS by 4.

If the answer in step 1716 is no, or after Step 1718, the program moves to step 1720. Step 1720 calculates the variable "transition" (T) as a function of variables OS and NS as shown in FIG. 17. Variable T provides a spectral quantification of the airway sounds for use in determining which action, if any, should be taken concerning the increase or decrease of the gas pressure applied to the respiratory passages of the patient. This determination occurs in step 1722 by use of a so-called action table" which is a look-up table stored in memory using variable T as a pointer. The preferred action table is incorporated as part of the disclosure hereof as Appendix I attached hereto.

Upon determining the proper action including increase, decrease, or maintain pressure from the action table, the program moves to step 1724 which executes that action. In the preferred embodiment, action-designated changes in pressure are in increments of 1.0 cm. water pressure.

If the action determined in step 1722 is "none", which indicates that snoring sounds are not occurring, it is preferred in step 1724 that the patient-applied the pressure be decreased by 0.5 cm. water. In this way, the program assures that the pressure is not maintained at a level greater than that necessary. For example, if the detected airway sounds prompts an increase in pressure, and the airway sounds then disappear, it may be that the pressure was increased slightly more than necessary. Accordingly, the program will automatically decrease the pressure over time in small increments until airway sounds are again detected.

The aspect of the present invention described above in connection with FIGS. 16 and 17 monitors airway sounds in the preferred embodiment. It will be appreciated, however, that pressure transducer circuit 700 is sensitive to many types of pressure variations other than those associated with airway sounds. For example, circuit 700 could be used to detect inaudible vibrations or pressure variations associated with exhalation and inhalation. With this capability, much information can be garnered about a patient's respiration such as whether the patient's respiration is rhythmic, erratic, or apneic as well as breath rate, inhalation and exhalation durations, and flow rates. Hence, with this capability the patient's respiration can be properly characterized and aspects of the respiration quantified.

Furthermore, this information can be stored in memory for subsequent downloading for use by a physician, for example, in diagnosing respiratory afflictions and efficacy of treatment. In this way the expense and time consumed in sleep lab facilities is avoided or at least minimized. Additionally, patient comfort is enhanced because only the minimum required pressure is imposed both during sleep and before the patient falls to sleep. With increased comfort, the patient is more likely to use the prescribed treatment on a sustained basis and thereby gain the maximum benefit therefrom.

As those skilled in the art will appreciate, the present invention encompasses many variations in the preferred embodiments described herein. For example while the present invention is useful in treating sleep apnea, its utility is not so limited, but rather, the present invention is useful in treating many conditions in which facilitated respiration is a factor in treatment. For example, increased respiratory air pressure beginning just prior to inhalation induces a deeper inhalation than might otherwise occur. This may be useful in treating certain cardiovascular conditions where deeper inhalation and thereby greater oxygenation of the blood is beneficial when accompanied by decreased pressure to ease exhalation. Additionally, the present invention encompasses the use of any breathable gas such as anesthesia or oxygen-supplemented ambient air.

As discussed above, the nasal pillow is the preferred means for patient coupling in order to impose the higher breathable gas pressure on the respiratory passages of the patient. The present invention, however, also encompasses a nasal mask, or a full face mask which may be desired in certain situations such as the application of anesthesia as breathable gas as discussed above.

In the preferred embodiment of the present invention, the position of the vent valve assembly is varied in order to increase or decrease the pressure of the breathable gas applied to the patient's respiratory passages. As the detailed description reveals, however, the apparatus hereof includes the capability of varying the speed of the blower unit which could be used instead to selectively vary the applied pressure. This would eliminate the need for the vent valve and stepper motor and reduce the manufacturing cost which would be advantageous as another embodiment of the invention.

The present invention also encompasses the variation wherein the breathable gas is compressed and stored in a storage bottle, for example.

As described above, the preferred controller includes microcontroller 802 which is operated by a computer program. Other equivalent control means might include a custom designed chip with all functions implemented in hardware without a computer program.

As disclosed in FIG. 6 herein and the accompanying narrative description, it is preferred to track the patient's breathing cycle by tracking the movement of vent valve assembly 16. Those skilled in the art will appreciate that the breath cycle can be tracked by other means such as monitoring chest contractions and expansion, breathing sounds, directly sensing genioglossus muscle activity, or some equivalent parameter indicative of a breathing cycle.

As a final example, some therapists may prefer that the apparatus start up in a low pressure or zero pressure mode while the breath cycle is initially tracked. This may provide further patient comfort in the use of the invention.

Admittance Embodiment

FIGS. 18–21 illustrate another embodiment of the present invention in which patient airway patency is determined and preferably used as the basis for controlling airway pressure applied to the patient. Turning initially to FIG. 18, apparatus 1800 includes flow sensor 1802 (Hans Rudolph Pneumotach available from the Hans Rudolph Company of Kansas City, Mo.), differential pressure (DP) sensor 1804 (SENSYM type SX01DN), pressure sensor 1806 (SENSYM type SX01DN), operational amplifiers 1808 and 1810, analog signal divider 1812 (Analog Devices model AD539) operably coupled with microcontroller 802.

In operation, flow sensor 1802 is preferably coupled in exterior portion 26 of conduit 12 so that breathable gas supplied to the patient passes therethrough. Sensor 1802 provides a pair of pneumatic output signals representative of the gas flow to DP sensor 1804 which in turn provides a pair of output electrical analog signals from the internal bridge representative of the flow to amplifier 1810.

Pressure sensor 1806 is pneumatically coupled with exterior portion 26 preferably downstream from flow sensor 1802. Pressure sensor 1806 provides a pair of signals from the internal bridge to amplifier 1808 representative of the gas pressure being supplied to the patient.

Amplifiers 1808 and 1810 provide respective analog output signals representative of the instantaneous gas pressure and flow being supplied to the patient by way of lines 1814 and 1816 to divider 1812. Divider 1812 performs an analog division of the flow and pressure signals presented on lines 1814, 1816 and thereby produces an analog output signal on line 1818 representative of the instantaneous admittance (A) of the patient's airway. That is to say, admittance is the inverse of impedance, but patient flow can be zero which prevents direct calculation of impedance as pressure divided by flow. However, by dividing flow by pressure, and thereby determining admittance, such problems are avoided.

As explained further hereinbelow in connection with the computer program flowchart of FIG. 21, it may be desirable to eliminate divider 1812 in certain applications and perform the division functions within microcontroller 802. If such is the case, line 1818 along with divider 1812 are eliminated, and the pressure and flow signals on lines 1814, 1816 are provided directly to microcontroller 802.

FIG. 19 includes graphs 1902, 1904, 1906, 1908, and 1910 which aid in illustrating how patient airway patency is determined in the present invention. These graphs respectively plot flow F, pressure P, admittance A, template T1, and template T2 versus seven discrete times corresponding to those times when microcontroller 802 performs analog-to-digital conversions of the input information. The plot of admittance in graph 1906 is a function of the flow and pressure data illustrated in graphs 1902, 1904 respectively.

In the operation of microcontroller 802 in accordance with the programs of FIGS. 20 and 21 the admittance plot for the inhalation portion of a single breath cycle is compared to admittance templates stored in memory to determine which template provides the "best fit" with the latest admittance plot. The best fit is determined by using conventional root-mean-square techniques. The template which fits best is used as a "pointer" for a look-up table to select action to be taken such as raising or lowering gas pressure delivered to the patient.

FIG. 20 illustrates a computer program flowchart of subroutine 2000 for operating microcontroller 802 of the embodiment shown in FIG. 18 using divider 1812. Routine 2000 enters at step 2002 which activates microcontroller 802 to digitize the admittance signal received on line 1818 at the predetermined times during patient inhalation and to store the converted admittance data in data array "A."

After all of the signals for inhalation signals have been digitized, step 2004 then normalizes the amplitudes of the amplitude data in array "A." That is to say, the peak-to-peak amplitude value of the array data is normalized to a predetermined constant. This is done because, in the preferred embodiment, the shape of the admittance data is of interest, not the absolute values.

Similarly, step 2006 normalizes the time base of the admittance data array "A" so that the time base matches that of the templates. This is needed because inhalation times vary from breathe to breathe.

The program then moves to step 2008 which computes a root-mean-square (RMS) value for the differences between the corresponding data points in array "A" and each template stored in memory according to the formula shown.

The program then moves to step 2010 which determines which template presents the lowest RMS value, this being the template that "best fits" the admittance data for that inhalation of the patient. Ssp 2012 then uses the template selected in step 2010 as a software "pointer" to select an appropriate action, such as increase, decrease or maintain pressure, from a look-up table such as that illustrated below:

| T1 | Maintain |
|----|----------|
| T2 | Increase |
| T3 | Increase |
| * | * |
| * | * |
| * | * |
| TN | Decrease |

FIG. 21 is a computer program flowchart of module 2100 for operating microcontroller 802 in the embodiment of FIG. 18 when divider 1812 and line 1818 are not used, and when lines 1814, 1816 are connected directly to microcontroller 802 for providing the pressure and flow signals. This variation is advantageous when greater precision is desired because of the non-linear characteristics of patient airways.

Module 2100 enters at step 2102 which digitizes the flow signals received by microcontroller 802 by way of line 1816 at the predetermined interval times. The digitized flow data is then stored in array "F". Step 2104 then normalizes the time base of the data in array "F."

The program then moves to step 2106 which uses Fast Fourier Transform (FFT) to convert the amplitude vs time data in array "F" to amplitude vs frequency data.

Simultaneous with steps 2102–2106, module 2100 executes analogous steps 2108, 2110 and 2112 for the pressure information received by microcontroller 802 over line 1814.

After the flow and pressure data have been convened, the program moves to step 2114 which computes admittance "A" for each corresponding flow and pressure data points. In some circumstances, depending upon the particular application and the level of accuracy desired, it may be advantageous to amplitude normalize the pressure and flow array data or the admittance data.

Module 2100 then executes 2116, 2118 and 2120 which are the same as steps 2008–2012 discussed above in connection with module 2000 and the action table.

It will be appreciated that after determination of the best-fit template, patient airway patency is effectively quantified. That is to say, the set of templates stored in memory could represent a range of patencies (in percentages, for example) and the best-fit template represents a corresponding patency as a percentage. Additionally, the patency templates are preferably a set custom-developed for the particular patient being treated. Furthermore, it may be advantageous to continuously update the set of templates by storing successive admittance array data in memory as a new template. Additionally, certain templates could be designated as templates characteristic of wakefulness or sleep states. Finally, in some circumstances the highest level of accuracy is not required, a summation of the admittance data of a given inhalation, or an average thereof over a number of inhalations, could be used itself as a quantification of airway patency.

Those skilled in the art will appreciate that the present invention encompasses many variations in the preferred embodiments described herein. For example, ultrasound techniques could be used to establish airway patency. Additionally, when the gas pressure applied to the patient is relatively constant, only flow variations are of interest and are the only variable parameter which may be considered. As a further example, a sensitive thermocouple or thermistor could be used as an indication of gas flow.

Stimulation Embodiment

As described above in connection with FIGS. 16 and 17, the spectral sounds embodiment of the present invention analyze the patient airway sounds to determine an appropriate response for preventing an apneic episode. In the spectral sounds embodiment, the appropriate action increases, decreases or maintains the airway pressure applied to the patient. In the stimulation embodiment, the preferred response is the application of electrical stimulus externally applied to the neck of the patient in the vicinity of the upper airway muscles, although implanted electrodes would be used equivalently to stimulate the muscles or the muscle nerves.

The preferred apparatus includes a flexible, elastic neck collar, a microphone carried by the collar, a pair of electrodes also carried by the collar, and control circuitry interconnecting the microphone and the electrodes. The electrodes and microphone could also be affixed by adhesive or other equivalent means instead of the preferred collar. The preferred control circuitry includes the components and program described above in connection with the airway sounds embodiment. The primary difference being that instead of increasing air pressure, the action is to activate the stimulating electrodes at the beginning of each inhalation phase of the patient breath cycle.

To use the stimulation embodiment, the patient couples the collar about the neck with the electrodes positioned in front about either side of the neck centerline and just underneath the jaw in order to stimulate the upper airway muscles when activated. In operation, the microphone detects airway sounds and the control circuitry analyzes these sounds as described above in connection with FIGS. 16 and 17. Whenever an action is determined corresponding to "increase" pressure (FIG. 17, Step 1724), this is interpreted as imminence of an apneic event. That is to say, gradual closing of the airway due to relaxation of the upper airway muscles produces sound patterns indicative thereof which also indicates, that is, predicts that an apneic episode may occur on a subsequent breath. Thus, when it is determined that an increase airway patency is needed, the control circuitry activates the electrodes to stimulate the upper airway muscles. Additionally, it is preferred to vary the strength of the electrical stimulation according to the breath sounds in the same manner that airway pressure is varied in connection with the admittance embodiment discussed above in connection with Appendix I. In the event that inhalation is not detected for a predetermined time based upon a fixed time or based upon previous breathing patterns the preferred breathing device activates the electrodes to stimulate the upper airway muscles.

In this way, apneic episodes are prevented while at the same time electrode stimulation is not imposed when not needed. This is in contrast to the prior art in which stimulation is not provided until an apneic episode has already occurred. This is also in contrast to those prior art devices which stimulate on each inhalation effort such as that set forth in U.S. Pat. No. 4,830,008, hereby incorporated by reference. As those skilled in the art can appreciate, if stimulation is applied with every inhalation, the patient effectively gets used to the stimulation and it is no longer as effective. The present invention, on the other hand, prevents stimulation when conditions are absent indicating, that is, predicting an apneic episode, but yet ensures stimulation before an apneic episode. Thus, the two main disadvantages of the prior art stimulation techniques are avoided.

As those skilled in the art can appreciate, other means can be used to detect the imminence of an apneic episode. For example, by monitoring airway admittance as discussed above in connection with FIGS. 19–21, an apneic episode can be predicted and stimulation applied when this occurs. That is to say, by monitoring admittance during inhalation, a narrowing of the airway can be detected by monitoring the admittance, and when admittance decreases to a predetermined level, stimulation can be applied. Furthermore, the imminence of an apneic episode could be determined by using airflow sensors such as thermistors or thermocouples at the nose or mouth, or a static-charge sensitive "bed", or bands for sensing chest or abdomen movement preferably a RESPITRACE brand sensor.

Compensation Embodiment

The preferred embodiment disclosed in FIGS. 1–4 uses pressure sensor 38 mounted adjacent the patient nasal fitting. In some circumstances, however, this may not be practical. Instead, for compactness and economy of manufacture, it may be desirable to use pressure and flow sensors coupled with the patient pneumatic line at the point where this line leaves cabinet 22. This arrangement, however, may allow inaccuracies in measurement to occur because of downstream pneumatic leaks and pressure drops in the line which vary nonlinearly with flow to the patient. In addition to unintended leaks, it is preferable to have a vent at the patient's nasal connection to prevent buildup of carbon dioxide. Thus, flow and pressure as measured at the cabinet outlet may not provide accurate data concerning the actual pressure delivered at the patient's nose. The compensation embodiment of the present invention measures pressure and flow at the cabinet outlet but still provides accurate measurement of the pressure presented to the patient by compensating for leaks and pressure drops.

FIG. 22 is a schematic block diagram illustrating the pneumatic system 70 which includes some components in common with those previously described and are numbered the same. System 70 additionally includes inlet air filter 71, exhalation solenoid 72 with exhalation valve 73 connected thereto, bacteria filter 74, flow element 75 with flow sensor 76 connected in parallel thereto.

FIG. 23 is an electrical block diagram illustrating the preferred components of controller 20 for controlling and operating pneumatic system 70 of this embodiment. Controller 20 includes power supply 80, microprocessor 81, microprocessor memory 82, analog to digital (A/D) conversion circuitry 83, interface circuitry 84, serial communication port 85 with remote control 86 connected thereto, keyboard and display control 87 with keyboard display panel 88 connected thereto.

FIGS. 24–31B are computer program flowcharts illustrating the operation of the program stored in memory 82 for operating microprocessor 81 and thereby for operating controller 20 and pneumatic system 70. FIG. 24 illustrates PRIMARY module 2400 which shows the overall arrangement and operation of the preferred program. PRIMARY module 2400 enters at step 2402 at power up when power supply 80 is activated. The program then executes INITIALIZE module 2500 (FIG. 25).

Step 2402 then asks whether the control mode is set to exhale or inhale. If set to inhale, step 2404 then asks whether the control mode has been set. If no, the program executes INHALE module 2700 (FIG. 27).

If the control mode has been set to exhale in step 2402, step 406 then asks whether the control mode has been set. If no, the program executes EXHALE module 2600 (FIG. 26).

If the answers in steps 2404 or 2406 are yes, or upon return from EXHALE and INHALE modules 2500 and 2600, the program moves to step 2408 which asks which backup mode has been selected. The program then executes the selected backup module illustrated in FIGS. 28–31B, after which the program loops back to step 2402. As FIG. 24 indicates, after initialization, the program operates alternatively through the exhale and inhale branches to set the respective exhale and inhale pressures and then proceeds to the selected backup module to determine whether backup operation is needed.

FIG. 25 illustrates INITIALIZE module 2500 which enters at step 2502 to set the variables indicated to their initial values as shown. Step 2504 then sets the pressure control mode to inhale and step 2506 clears the control mode flag indicating that the control mode has not been set.

Steps 2508 and 2510 then set the flow bias (Fbias) variables for inhale and exhale for the amounts corresponding to the vent or bleed hole present in the preferred nasal pillow shell used for connection with the patient airways. Step 2512 then reads the prescribed pressure settings set on switch 814 (FIG. 8).

Next, step 2514 sets a software flag indicating that the next analog to digital interrupt will read pressure transducer data (when not set, the A/D interrupt reads flow transducer data). An A/D conversion for pressure is then immediately executed in step 2516.

Blower 18 is then started at a speed sufficient to produce the prescription pressure setting. The program then returns to step 2402 (FIG. 24).

FIG. 26 illustrates EXHALE module 2600 which is entered when the exhale branch of PRIMARY module 2400 detects that the exhale flag has been set. Module 2600 enters at step 2602 which sets the patient pressure at the exhale prescription pressure. Step 2604 then opens exhalation valve 73 by activating exhalation solenoid 72.

The phase control flags are then reset in step 2606 and the blanking interval counter cleared in step 2608. The program then returns to the PRIMARY module.

FIG. 27 illustrates INHALE module 2700 which is entered at the beginning of inhalation and which is repeatedly executed during patient inhalation. Module 2700 enters at step. 2702 which sets the total breath count to the sum of the exhale and inhale sample counts. As discussed further hereinbelow, each inhalation and exhalation is counted and this step takes the sum of these counts to determine a value which is used as the total breath count.

Step 2704 then asks whether a backup mode has been indicated as discussed further hereinbelow. If no, step 2706 calculates a value for average breath as illustrated. With this step, patient breathing rate is tracked. If the answer in step 2704 is yes, the average breath rate is set as equal to the previous average breath in step 2708.

After steps 2706 or 2708, step 2710 calculates the average breath volume according to the formula shown. Step 2712 then determines the maximum exhalation duration and step 2714 determines a value representative of the pneumatic leaks occurring during inhalation. Steps 2710–2714 use values for these calculations which are explained further hereinbelow.

Step 2716 then asks whether the current peak blower inlet valve (BIV) position is less than 100. If yes, step 2718 decrements the blower speed. In other words, if the blower is supplying excessive air, the blower speed is decreased. If the answer in step 2716 is no or after step 2718, step 2720 asks whether the current peak BIV position is greater than 130. The difference between 130 in this step and 100 in step 2716 provides a dead zone so that the program does not continuously hunt for a stable value. If the answer in step 2720 is yes, step 2722 asks whether the current blower speed is below the maximum speed. If yes, step 2724 increments the blower speed in order to supply more air.

After step 2724 or if the answers in steps 2720 or 2722 are no, step 2726 then sets the pressure control set point to the exhale prescription pressure and step 2728 then opens exhalation valve 73 by activating exhalation solenoid 72. The phase control flags are then reset in step 2730 and the peak BIV position variable flag is cleared in step 2732. Next, step 2734 clears the blanking interval counter and the program returns to step 2408 (FIG. 24).

FIGS. 28–30 illustrate the three selectable backup modes which are executed if inhalation is not detected within a time limit based on breath rate. In the CPAP mode (FIG. 28), the pressure is increased to a constant value and maintained. In the BPM backup mode (FIG. 29), the patient pressure is increased to a high level and maintained until the earliest occurrence of sensed exhalation or a time correlated with previous breath rates. The patient backup mode (FIG. 30) results in a high pressure being delivered to the patient for a fixed time not based on previous breath rates, or when exhalation is sensed, whichever occurs first.

Turning first to FIG. 28, CPAP BACKUP module 2800 enters at step 2802 which asks whether the backup test is true. More particular, this step asks whether the pressure control mode is set for exhale, the backup flag is clear, and the count on the exhale timer is greater than the average of the last three exhale periods plus five seconds. If all of these conditions are true, then the answer in step 2802 is yes. The program then moves to step 2804 which sets the pressure control mode to inhale and then in step 2806 sets the backup flag as true.

If any of the required conditions for step 2802 is not satisfied, then the answer in step 2802 is no and the program moves to step 2808 which asks whether the backup flag is set. If yes, step 2810 asks whether the count on the backup timer is greater than the minimum allowable time which in this step is the average of the last three inhalation periods (see steps 2706 and 2708). If the answer in step 2810 is yes, step 2812 clears the backup flag. After steps 2806 or 2812, or if the answers in steps 2808 or 2810 are no, the program returns to step 2408 (FIG. 24).

BPM BACKUP module 2900 (FIG. 29) enters at step 2902 which asks whether the backup flag is clear. If yes, step 2904 asks whether the inhale timer count is greater than or equal to the maximum allowable inhalation time which is 60 divided by the BPM dial setting and this quantity times the fixed inhalation to exhalation ratio (typically 1:1.5). If yes, step 2906 sets the pressure control mode to exhale and step 2908 sets the backup flag as true.

If the answer in step 2902 is no, step 2910 asks whether the count on the backup timer is greater than or equal to the minimal allowable time which is the same value as that determined in step 2904. If yes, step 2912 clears the backup flag.

If the answer in step 2904 is no, step 2914 asks whether the exhale timer count is greater than or equal to the maximal allowable exhalation time which is 60 divided by the BPM setting quantity divided by the inhalation/exhalation ration. If yes, step 2916 sets the pressure control mode to inhale as step 2918 sets the backup flag as true. After steps 2908, 2912 or 2918, or if the answers in steps 2910 or 2914 are no, the program returns to step 2408 (FIG. 24).

FIG. 30 illustrates PATIENT BACKUP module 3000 which enters at step 3002. This step asks whether the backup flag is clear and if yes, the program moves to step 3004 which asks whether the inhale timer count is greater than or equal to the time duration of the last inhalation. If yes, step 3006 sets the pressure control mode to exhale and step 3008 sets the backup flag as true.

If the answer in step 3002 is no, step 3010 asks whether the count on the backup timer is greater than or equal to the minimal allowable time which is the last inhalation time as determined by the inhalation counter (see step 3158). If yes, step 3012 clears the backup flag.

If the answer in step 3004 is no, step 3014 asks whether the exhale timer count is greater than or equal to the time duration of the last exhale. If yes, step 3016 sets the pressure control mode to inhale and step 3018 then sets the backup flag as true. After steps 3008, 3012 or 3018, or if the answers in step 3010 or 3014 are no, the program returns to step 2408 (FIG. 24).

FIGS. 31A–B illustrate A/D INTERRUPT module 3100 which is executed every 14 milliseconds. This module enters at step 3102 which asks whether the last conversion was executed for pressure or flow. If pressure, step 3104 retrieves the A/D value for pressure sensor 38 which value was previously stored during the last conversion for pressure. Step 3106 then initiates A/D conversion for flow sensor 76 and the interrupt ends.

If the last conversion was for flow as determined in step 3102, step 3108 then retrieves the previously stored flow sensor value. This value is then linearized according to look-up table values stored in memory which are empirically developed for the particular patient pneumatic hose 26 being used. In practice, units include standard hose links so that the look-up table values do not need to be redeveloped.

Step 3112 then determines the pressure drop in patient hose 26 on the basis of linear flow according to techniques well known to those skilled in the art. The pressure deviation from the prescription set point is then determined in step 3114. This deviation is the pressure error (Pe) determined by subtracting the pressure drop which is the pressure at the patient's nose (Pn) less the pressure drop in the hose at the flow rate (Pdrop) quantity subtracted from the prescription set point.

Step 3116 then asks whether the pressure error is greater than 2. If yes, step 3118 opens the blower inlet valve 46 one position. If the answer to step 3116 is no, step 3120 asks whether the pressure error is less than –2. If yes, step 3122 closes blower inlet valve 46 one position. The span between +2 in step 3116 and –2 in step 3120 provides a dead zone to prevent hunting for a stable position.

After steps 3118 or 3122, or if the answer in step 3120 is no, the program moves to step 3124 which increments the variable "volume sum" with the current flow value. In this way, the total volume delivered to the patient is determined by adding the sum of periodically stored instantaneous flows delivered to the patient. These values are determined at equal time intervals and in this way to total volume delivered equals the sum of the flow values.

Step 3126 then increments the backup timer counter by one. Next, step 3128 increments the sample counter and blanking interval counter each by one. Step 3130 then asks whether the backup flag is set. If yes, step 3132 increments the backup timer by one.

If the answer in step 3130 is no, step 3134 (FIG. 31B) asks whether the blanking interval counter is greater than its predetermined allowable limit (preferably 1.4 seconds which is 100 counts of the interrupt return every 0.014 seconds). If the answer in step 3134 is yes, step 3136 then asks whether the pressure control mode is set to exhale. If yes, step 3138 then asks whether the current flow value is greater than or equal to the exhale flow bias (the predetermined amount of air lost through the vent) plus the amount of leakage occurring during inhalation.

If the answer in step 3138 is yes, step 3140 sets the Prx which is the control mode to inhale. Step 3142 then clears the blank interval counter, step 3144 saves the current sample count and step 3146 clears the sample counter.

If the answer in step 3136 is no, step 3148 asks whether the pressure control mode is set to inhale. If yes, step 3150 asks whether the current flow is less than or equal to the vent flow bias during inhale plus the leakage during exhale. If this condition is true, step 3152 sets the Prx control mode flag for exhale. Step 3154 then clears the blank interval counter after which step 3155 clears the volume sum counter and step 3156 saves the current value for volume sum. Step 3156 then resets the variable volume sum to zero, step 3158 saves the current sample count, and step 3160 clears the sample counter.

If the answers are no in steps 3130, 3134–3138 or 3148–3150, or after steps 3146 or 3160, the program moves to step 3162 which initiates an A/D conversion for the pressure transducer. A/D INTERRUPT module 3100 then ends.

APPENDIX I
ACTION TABLE
Sounds State Transition Matrix

| # | To: (new) | 0 | 1 | 2 | 3 | 4 | 5 | 6 | 7 |
|---|---|---|---|---|---|---|---|---|---|
| | Hi | | 0 | 0 | 0 | 0 | 1 | 1 | 1 | 1 |
| From: | Med | | 0 | 0 | 1 | 1 | 0 | 0 | 1 | 1 |
| (old) | Low | 0 | 1 | 0 | 1 | 0 | 1 | 0 | 1 |
| 0 | 0 | 0 | 0 | 0 | 1 | 2 | 3 | 4 | 5 | 6 | 7 |
| 1 | 0 | 0 | 1 | 8 | 9 | 10 | 11 | 12 | 13 | 14 | 15 |
| 2 | 0 | 1 | 0 | 16 | 17 | 18 | 19 | 20 | 21 | 22 | 23 |
| 3 | 0 | 1 | 1 | 24 | 25 | 26 | 27 | 28 | 29 | 30 | 31 |
| 4 | 1 | 0 | 0 | 32 | 33 | 34 | 35 | 36 | 37 | 38 | 39 |
| 5 | 1 | 0 | 1 | 40 | 4 | 42 | 43 | 44 | 45 | 46 | 47 |
| 6 | 1 | 1 | 0 | 48 | 49 | 50 | 51 | 52 | 53 | 54 | 55 |
| 7 | 1 | 1 | 1 | 56 | 57 | 58 | 59 | 60 | 61 | 62 | 63 |

| State | Description of Comments | |
|---|---|---|
| 0 | No Sound | |
| 1 | Smooth Snoring | [ssnore] |
| 2 | Other (talking) | [other] |
| 3 | Turbulent Snoring | [tsnore] |
| 4 | Start of clearing an obstruction | [sclob] |
| 5 | Partial obstruction | [parob] |
| 6 | Clearing an obstruction | [clob] |
| 7 | Raucous Snoring | [rsnore] |

| Transition | Action | Comments |
|---|---|---|
| 0 | Decrease | No sounds |
| 151 | Increase | Start of ssnore |
| 2 | None | Start of other |
| 3 | Increase | Start of tsnore |
| 4 | Increase | Start of sclob |
| 205 | Increase | Start of parob |
| 6 | Increase | Start of clob |
| 7 | Increase | Start of rsnore |
| 8 | None | End of ssnore |
| 259 | Increase | Ssnore continues |
| 10 | None | End of ssnore |
| 11 | Increase | Ssnore to tsnore-airway narrowing? |
| 12 | Increase | Airway narrowing? |
| 13 | Increase | Airway narrowing? |
| 14 | Increase | Airway narrowing? |
| 15 | Increase | Airway narrowing? |
| 16 | None | End of other |
| 17 | Increase | Airway opening? |
| 18 | None | Other |
| 19 | Increase | Probable tsnore cont. |
| 20 | Increase | Clob |
| 21 | Increase | Clob |
| 22 | Increase | Clob |
| 23 | Increase | Rsnore |
| 24 | None | End of tsnore |
| 25 | Increase | Tsnore to ssnore |
| 26 | Increase | Airway narrowing? Airflow decreasing? |
| 27 | Increase | Tsnore |
| 28 | Increase | Airway narrowing? Airflow increasing? |
| 29 | Increase | Airway narrowing? Airflow decreasing? |
| 30 | Increase | Airway narrowing? Airflow decreasing? |
| 31 | Increase | Airway narrowing? Airflow increasing? |
| 32 | None | |
| 33 | Increase | Airway opening post obstruction |
| 34 | Increase | Airway opening post obstruction |
| 35 | Increase | Airway opening post obstruction |
| 36 | None | |
| 37 | Increase | |
| 38 | Increase | |
| 39 | Increase | Airway opening post obstruction |
| 40 | None | |
| 41 | Increase | |
| 42 | Increase | |
| 43 | Increase | Airway opening post obstruction |
| 44 | Increase | |
| 45 | Increase | Partially obstructed snore |
| 46 | Increase | |
| 47 | Increase | Airway opening post obstruction |
| 48 | None | |
| 49 | Increase | Airway opening post obstruction |
| 50 | Increase | Airway opening post obstruction |
| 51 | Increase | Airway opening Airflow decreasing |
| 52 | Increase | Airflow increasing |
| 53 | Increase | |
| 54 | Increase | |
| 55 | Increase | Airway opening post obstruction |
| 56 | None | |
| 57 | Increase | Airway opening |
| 58 | Increase | Airflow decreasing |
| 59 | Increase | Airway opening |
| 60 | Increase | Airway narrowing? Airflow increasing? |
| 61 | Increase | |
| 62 | Increase | |
| 63 | Increase | |

We claim:

1. An apparatus for determining the airway patency of a patient exhibiting a breath cycle having inhalation and exhalation phases, said apparatus comprising:

means for supplying a breathable gas from a source thereof under a controllable pressure to at least a portion of the patient's airway, said pressure being maintained substantially constant during the inhalation phase of a breath cycle;

means for sensing patient respiration flow and for producing flow signals representative of patient respiration flow;

signal processing means for receiving said flow signals and for determining patient airway patency values from said flow signals in view of said pressure of breathable gas delivered by said means for supplying; and means for adjusting said pressure in accordance with said patient airway patency values.

2. The apparatus as set forth in claim 1, said breathable gas including ambient air.

3. The apparatus as set forth in claim 1, said sensing means including flow sensor means for sensing patient respiration flow and for producing signals representative thereof.

4. The apparatus as set forth in claim 3, said flow sensor means including a differential pressure flow sensor.

5. The apparatus as set forth in claim 1, said signal processing means including first means for storing into memory at least one airway patency template composed of a plurality of airway patency values, second means for storing into memory a set of patient airway patency values, and means for comparing said set of patient airway patency values with said at least one stored airway patency template.

6. The apparatus as set forth in claim 5, said first means for storing including a plurality of stored templates, said signal processing means further including means for determining which of said templates presents the closest match with said set of patient airway patency values, said closest match being representative of patient airway patency.

7. The apparatus as set forth in claim 6, said controlling means including means for controlling said pressure in accordance with said closest match.

8. The apparatus as set forth in claim 6, said templates presenting normalized amplitudes and time bases, said signal processing means further including means for normalizing the amplitude and time base of said patient airway patency values in accordance with said stored templates.

9. The apparatus as set forth in claim 6, said controlling means including a microprocessor.

10. The apparatus as set forth in claim 1, said patient airway patency values being determined as a function of said flow signals during a patient inhalation.

11. The apparatus as set forth in claim 1, said controlling means including a microprocessor.

12. The apparatus as set forth in claim 1, said signal processing means including means for using Fast Fourier Transforms for processing said flow signals representative of said patient respiration flow.

13. A method of determining the airway patency of a patient, the patient exhibiting a breath cycle having inhalation and exhalation phases, said method comprising:

using sensing means for repeatedly sensing a plurality of patient respiration flows being maintained under substantially constant pressure during a patient inhalation phase and for producing flow signals representative thereof;

using signal processing means for receiving said flow signals and responding thereto for determining a set of patient airway patency values from said flow signals in view of said pressure of breathable gas delivered by said means for supplying and storing patient airway patency data representative of said set of patient airway patency values in a memory device, and using said signal processing means for determining said patient airway patency values from said flow signals;

comparing in said signal processing means said patient airway patency data with predetermined airway patency templates stored in said memory device; and determining in said signal processing means the closest match of said airway patency templates with said patient airway patency data, said closest match being representative of patient airway patency during said phase.

14. The method as set forth in claim 13, said step of determining patient airway patency data including the step of using Fast Fourier Transforms for processing data representative of said flow signals.

15. The method as set forth in claim 13 further including the steps of supplying the patient with a breathable gas from a source thereof under a controllable pressure to at least a portion of the patient's airway; and controlling said gas pressure in accordance with said patient airway patency.

16. The method as set forth in claim 13, further including the steps of:

storing in a memory device a set of pressure change actions corresponding to said templates; and executing an action corresponding to said template presenting the closest match to said patient airway patency data.

17. An apparatus for determining the airway patency of a patient, the apparatus comprising:

means for repeatedly sensing a plurality of patient respiration flows being maintained under substantially constant pressure and for producing flow signals representative thereof;

signal processing means for receiving said flow signals and for determining a set of patient airway patency values from said flow signals in view of said pressure being maintained substantially constant; and memory means for storing a plurality of airway patency templates representative of a plurality of predetermined airway patency data arrays, said signal processing means including means for determining which of said airway patency templates presents the closest matching airway patency to said set of patient airway patency values, the matching airway patency template being representative of the patient's airway patency.

18. An apparatus for the treatment of obstructive sleep apnea in a patient having an airway, the apparatus comprising:

a source of breathable gas;

means for maintaining an inspiratory gas flow from said source to a patient airway, and for maintaining a relatively constant pressure at the airway;

means for generating inspiratory flow signals representative of the inspiratory gas flow to the airway in view of said pressure being maintained relatively constant;

means for comparing the inspiratory flow signals to a template of flow values representative of an obstruction in the airway; and means for adjusting the pressure at the airway, wherein the pressure is increased when comparing the inspiratory flow signals to the template of flow values indicates patient airway obstruction, and wherein the pressure is decreased when comparing the inspiratory flow signals to the template of flow values does not indicate patient airway obstruction.

19. A method for controlling the positive airway pressure to a patient, the method comprising the steps of:

generating inspiratory flow signals representative of the inspiratory airflow to a patient when the change in airway pressure is sensed to be approximately zero;

comparing the inspiratory flow signals to a template of flow values representative of patient airflow obstruction in view of the change in said pressure being sensed to be approximately zero;

increasing the airway pressure when the comparison of the inspiratory flow signals to the template of flow values indicates patient airway obstruction; and decreasing the airway pressure when the comparison of the inspiratory flow signals to the template of flow values does not indicate patient airway obstruction.

20. The method as set forth in claim 19, said step of increasing the airway pressure including rapidly adjusting the pressure to prevent obstruction during a subsequent inspiration phase, and said step of decreasing the airway pressure including slowly adjusting the pressure to prevent obstruction during a subsequent inspiration phase.

21. A method of determining the airway patency of a patient, the patient exhibiting a breath cycle having an inhalation phase of substantially constant airway pressure, the method comprising:

sensing a plurality of patient respiration flows during a patient inhalation phase;

generating flow signals representative of the patient respiration flows when the change in airway pressure is sensed to be about zero;

determining patient airway patency values from said flow signals;

comparing the patient airway patency values with predetermined patient airway patency templates in view of the change in said pressure being sensed to be about zero; and determining the template having the best fit with the patient airway patency values, wherein the template having the best fit is representative of patient airway patency during the patient inhalation phase.

22. The method as set forth in claim 21, further comprising the steps of:

increasing the airway pressure when the template having the best fit represents patient airway obstruction; and decreasing the airway pressure when the template having the best fit does not represent patient airway obstruction.

* * * * *

UNITED STATES PATENT AND TRADEMARK OFFICE
CERTIFICATE OF CORRECTION

PATENT NO. : 5,549,106
DATED : Aug. 27, 1996
INVENTOR(S) : Roger A. Gruenke, Russell L. Trimble It is certified that error appears in the above-indentified patent and that said Letters Patent is hereby corrected as shown below:

Column 2, Line 20, change "CFAP", to read --CPAP--.

Column 4, Line 49, after "18;", delete "and".

Column 4, Line 52, change "18.", to read --18;--.

Column 9, Line 3, change "(0.005nF)", to read --(0.005µF)--.

Column 13, Line 60, change "cycle", to read --cycles--.

Column 18, Line 39, after "For example", add --,--.

Column 27, APPENDIX I, Line 24, move "Low" to the right one column.

Column 27, APPENDIX I, Line 24, move "0 1 0 1 0 1 0 1" right one column.

Column 27, APPENDIX I, Line 30, change " 4", to read --41--.

Column 27, APPENDIX I, Line 44, change "151", to read --1--.

Column 27, APPENDIX I, Line 48, change "205", to read --5--.

Column 27, APPENDIX I, Line 51, change "259", to read --9--.

Column 29, Claim 15, Line 55, after "step of", add --:--.

UNITED STATES PATENT AND TRADEMARK OFFICE
CERTIFICATE OF CORRECTION

PATENT NO. : 5,549,106
DATED : Aug. 27, 1996
INVENTOR(S) : Roger A. Gruenke, Russell L. Trimble It is certified that error appears in the above-indentified patent and that said Letters Patent is hereby corrected as shown below:

FIG. 21, Sheet 11 of 21, Item 2114, after "F(i)", add -- $\div$ --.

Signed and Sealed this

Eighth Day of July, 1997

Attest:

BRUCE LEHMAN

Attesting Officer    Commissioner of Patents and Trademarks